(12) United States Patent
Smith et al.

(10) Patent No.: US 11,160,518 B2
(45) Date of Patent: Nov. 2, 2021

(54) METHODS AND SYSTEMS FOR INTEGRATED FILTER SYSTEM

(71) Applicant: GE Precision Healthcare LLC, Milwaukee, WI (US)

(72) Inventors: Brandon Allan Smith, Waukesha, WI (US); Timothy Mathew Behlmer, Milwaukee, WI (US); Dominic Joseph Crotty, Waukesha, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 0 days.

(21) Appl. No.: 16/543,448

(22) Filed: Aug. 16, 2019

(65) Prior Publication Data

US 2021/0045702 A1 Feb. 18, 2021

(51) Int. Cl.
*A61B 6/00* (2006.01)
*G21K 1/10* (2006.01)

(52) U.S. Cl.
CPC .......... *A61B 6/4035* (2013.01); *A61B 6/4447* (2013.01); *G21K 1/10* (2013.01)

(58) Field of Classification Search
None
See application file for complete search history.

(56) References Cited

U.S. PATENT DOCUMENTS

| | | | |
|---|---|---|---|
| 6,307,918 B1 * | 10/2001 | Toth | A61B 6/032 378/156 |
| 8,238,522 B2 | 8/2012 | Frey et al. | |
| 8,503,615 B2 | 8/2013 | Hockersmith et al. | |
| 9,220,466 B2 | 12/2015 | Liu et al. | |
| 2002/0037067 A1 | 3/2002 | Horiuchi | |
| 2007/0025520 A1 * | 2/2007 | Thandiackal | A61B 6/032 378/157 |
| 2010/0142680 A1 | 6/2010 | August | |
| 2011/0033030 A1 | 2/2011 | Loos | |
| 2011/0249787 A1 | 10/2011 | Frey | |

(Continued)

FOREIGN PATENT DOCUMENTS

WO 2009096361 A1 8/2009

OTHER PUBLICATIONS

Thibault, J. et al., "Methods and Systems for X-Ray Tube Conditioning," U.S. Appl. No. 16/543,468, filed Aug. 16, 2019, 60 pages.

(Continued)

*Primary Examiner* — Hoon K Song

(57) ABSTRACT

Various methods and systems are provided for an integrated filter assembly including a plurality of bowtie filters and a hardening filter mounted on a single carriage. In one embodiment, an imaging system may include a carriage including a hardening filter and one or more bowtie filters, and a filter driving system for moving the carriage to selectively position the hardening filter and one of the one or more bowtie filters in a path of a radiation beam between a radiation source and an imaging subject, the hardening filter at least partially overlapping with at least one of the one or more bowtie filters. In this way, a single carriage may include a plurality of filters which may be selectively positioned in a path of the radiation beam entering a subject without having to stack multiple carriages and switch carriages between scans.

20 Claims, 14 Drawing Sheets

(56) References Cited

U.S. PATENT DOCUMENTS

2014/0376689 A1 12/2014 Zou
2018/0168524 A1 6/2018 Melman

OTHER PUBLICATIONS

Crotty, D. et al., "Methods and Systems for X-Ray Tube Conditioning," U.S. Appl. No. 16/543,474, filed Aug. 16, 2019, 61 pages.
EP application 20188938.3 filed Jul. 31, 2020—extended Search Report dated Oct. 14, 2020; 6 pages.

\* cited by examiner

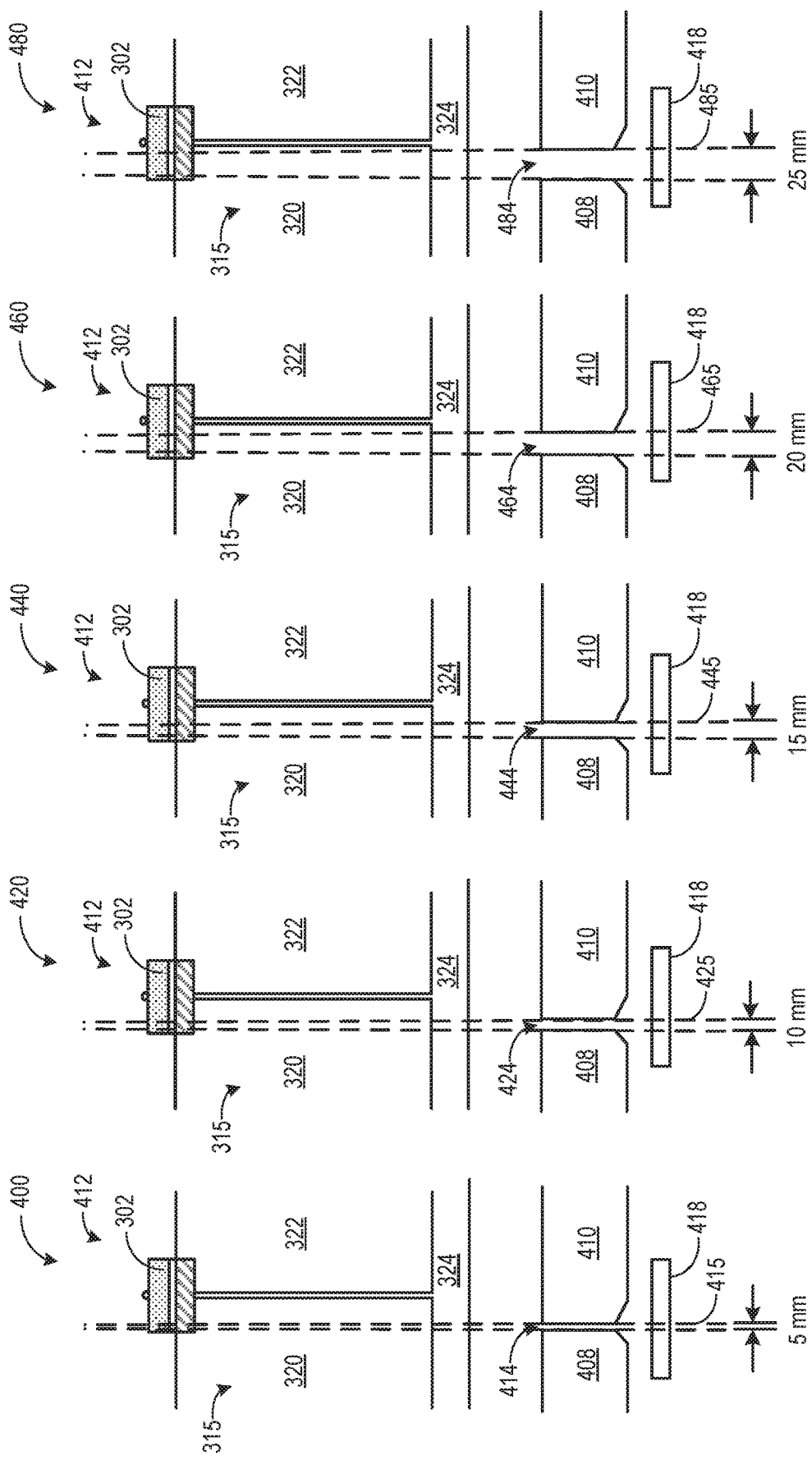

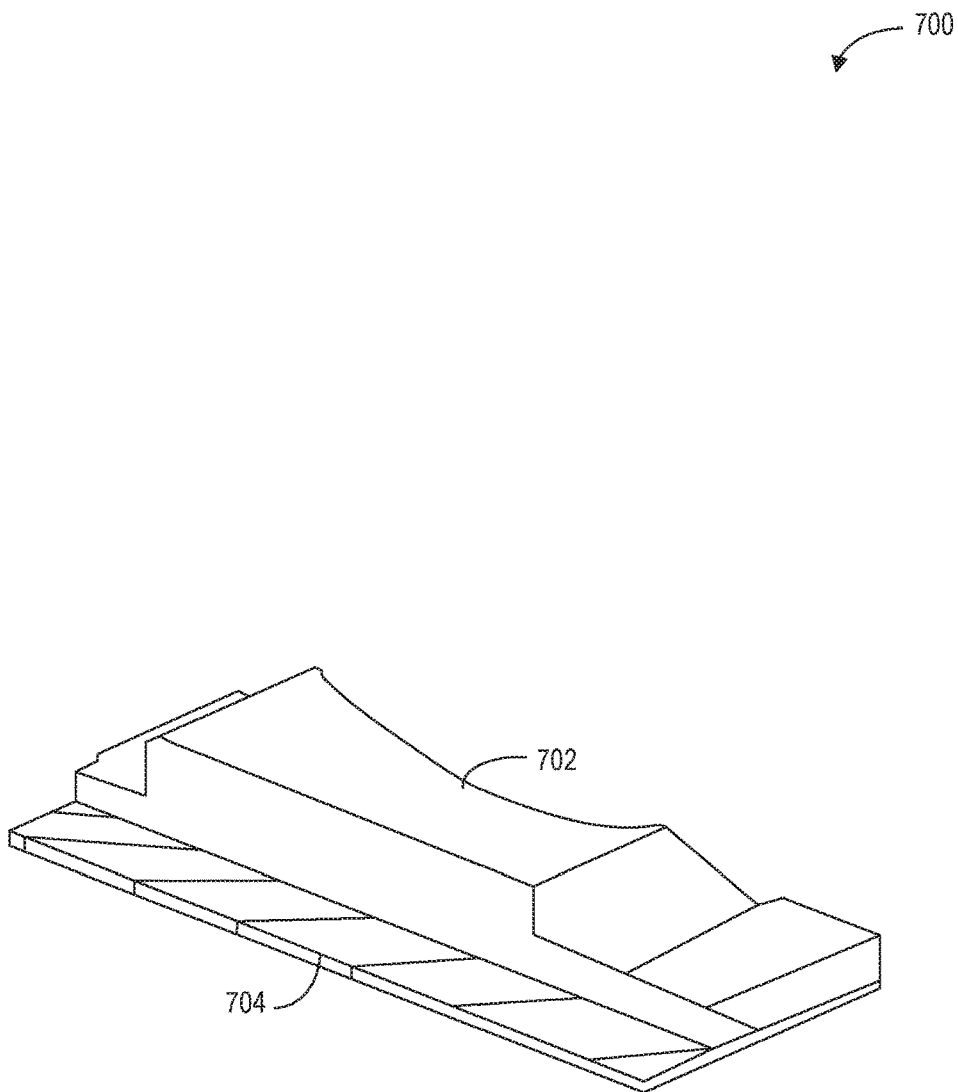
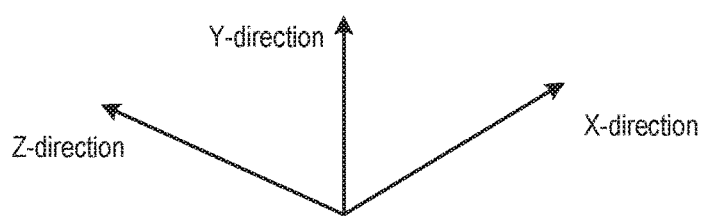
FIG. 7

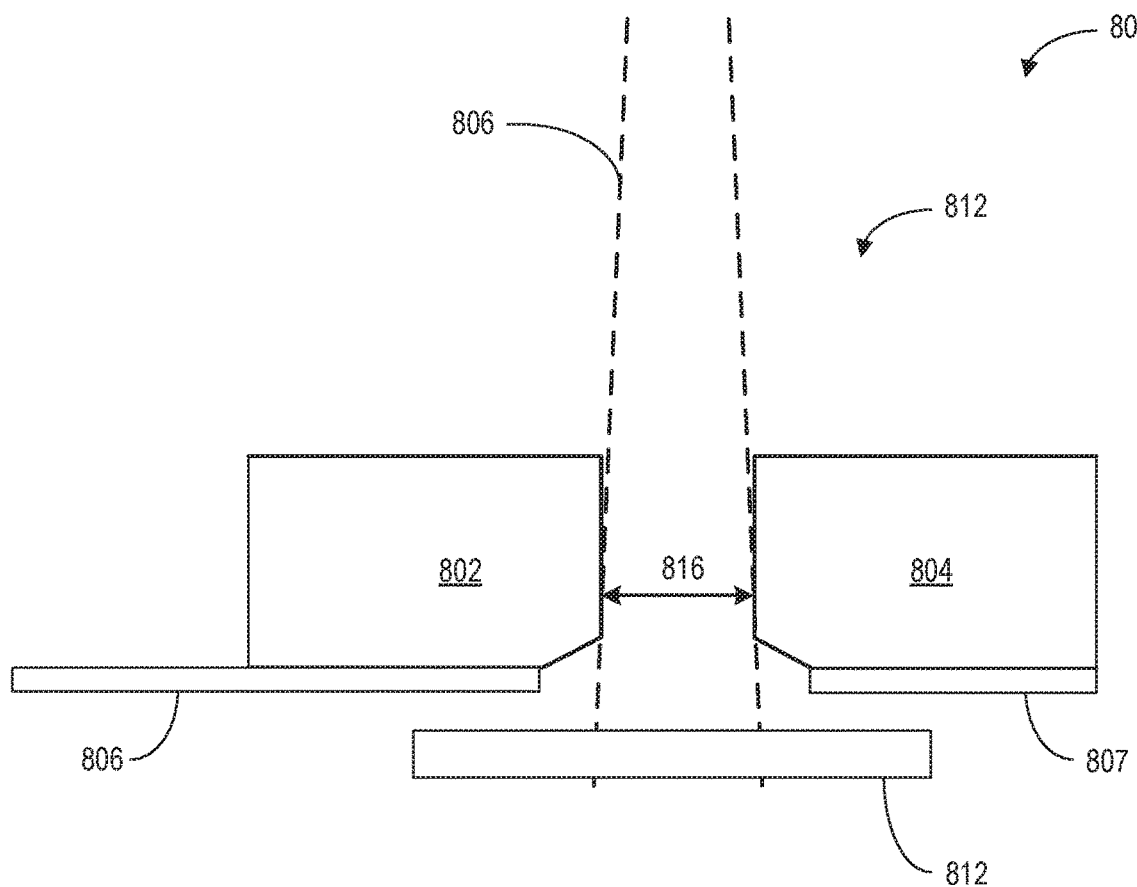
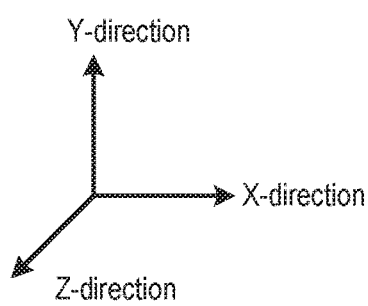
FIG. 8A

METHODS AND SYSTEMS FOR INTEGRATED FILTER SYSTEM

FIELD

Embodiments of the subject matter disclosed herein relate to diagnostic medical imaging, and more particularly, to computed tomography imaging setup with an integrated filter assembly.

BACKGROUND

Noninvasive imaging modalities may transmit energy in the form of radiation into an imaging subject. Based on the transmitted energy, images may be subsequently generated indicative of the structural or functional information internal to the imaging subject. In computed tomography (CT) imaging, radiation transmits from a radiation source to a detector through the imaging subject. A bowtie filter may be positioned between the radiation source and the imaging subject for adjusting the spatial distribution of the radiation energy based on the anatomy of the imaging subject. The bowtie filter may be designed to distribute higher radiation energy to specific imaging region of the subject. As a result, the amplitude of signal received by the imaging detector is improved, and the radiation dose on the periphery of the specific imaging subject is reduced. Different anatomy of the subject may require different bowtie filters. For example, bowtie filters of different shape and size may be designed to image distinct regions of the subject's body such as the head, the chest, and the abdomen.

Further, a hardening filter may be positioned between the radiation source and the imaging subject for intercepting the lower energy radiations, thereby attenuating and "hardening" the beam. Conditioning of the beam via a hardening filter may be specifically desired during a scout scan which may precede a diagnostic scan and may provide a projection view along a longitudinal axis of the subject including the internal structure of the subject. Therefore, a setup for integrating one or more bowtie filters and a hardening filter is needed.

BRIEF DESCRIPTION

In one embodiment, a system comprises a carriage including one or more hardening filters and one or more bowtie filters, and a filter driving system for moving the carriage to selectively position the one or more hardening filters and one of the one or more bowtie filters in a path of a radiation beam between a radiation source and an imaging subject, the one or more hardening filters at least partially overlapping with at least one of the one or more bowtie filters.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below:

FIG. 4A shows a collimation arrangement for an x-ray beam of a first size.

FIG. 4B shows the collimation arrangement of FIG. 4A for an x-ray beam of a second size.

FIG. 4C shows the collimation arrangement of FIG. 4A for an x-ray beam of a third size.

FIG. 4D shows the collimation arrangement of FIG. 4A for an x-ray beam of a fourth size.

FIG. 4E shows the collimation arrangement of FIG. 4A for an x-ray beam of a fifth size.

FIG. 7 shows a collimator blade including a blocking plate.

FIG. 8A shows a first position of a collimation arrangement for an x-ray beam including a blocking plate.

DETAILED DESCRIPTION

Figure 1:
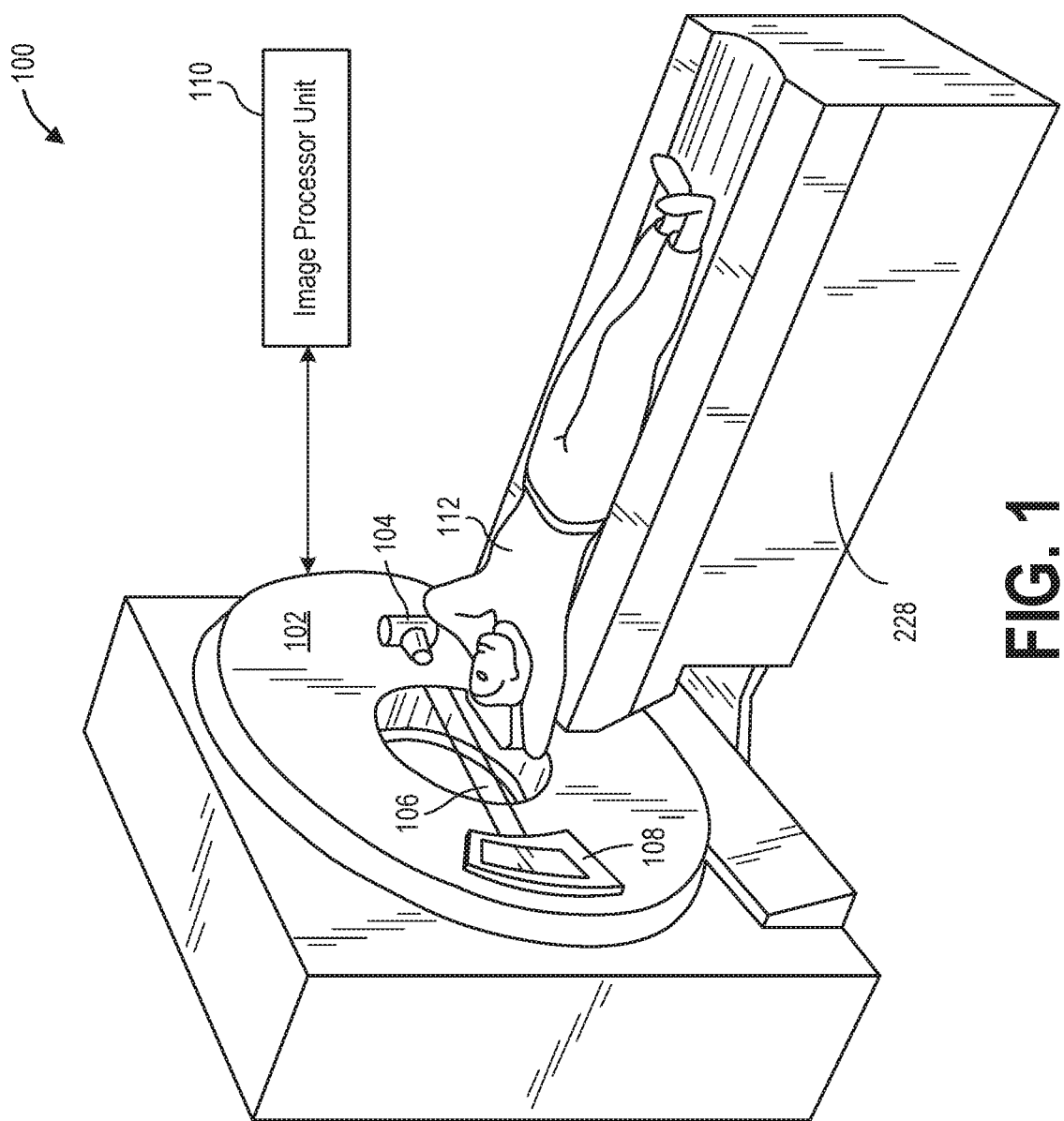
FIG. 1 shows a pictorial view of an imaging system according to an embodiment of the invention.
Figure 2:
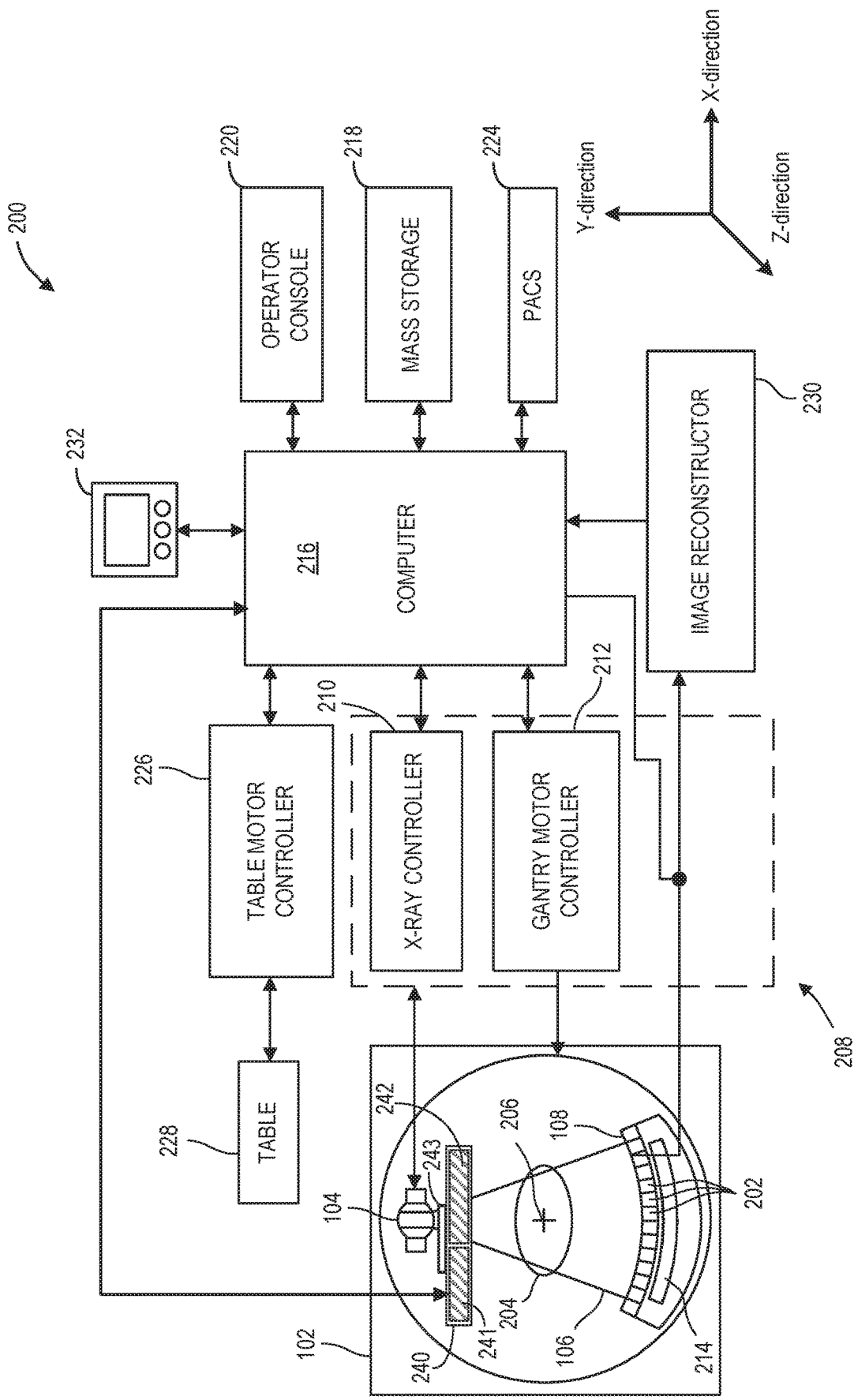
FIG. 2 shows a block schematic diagram of an exemplary imaging system according to an embodiment of the invention.
Figure 3:
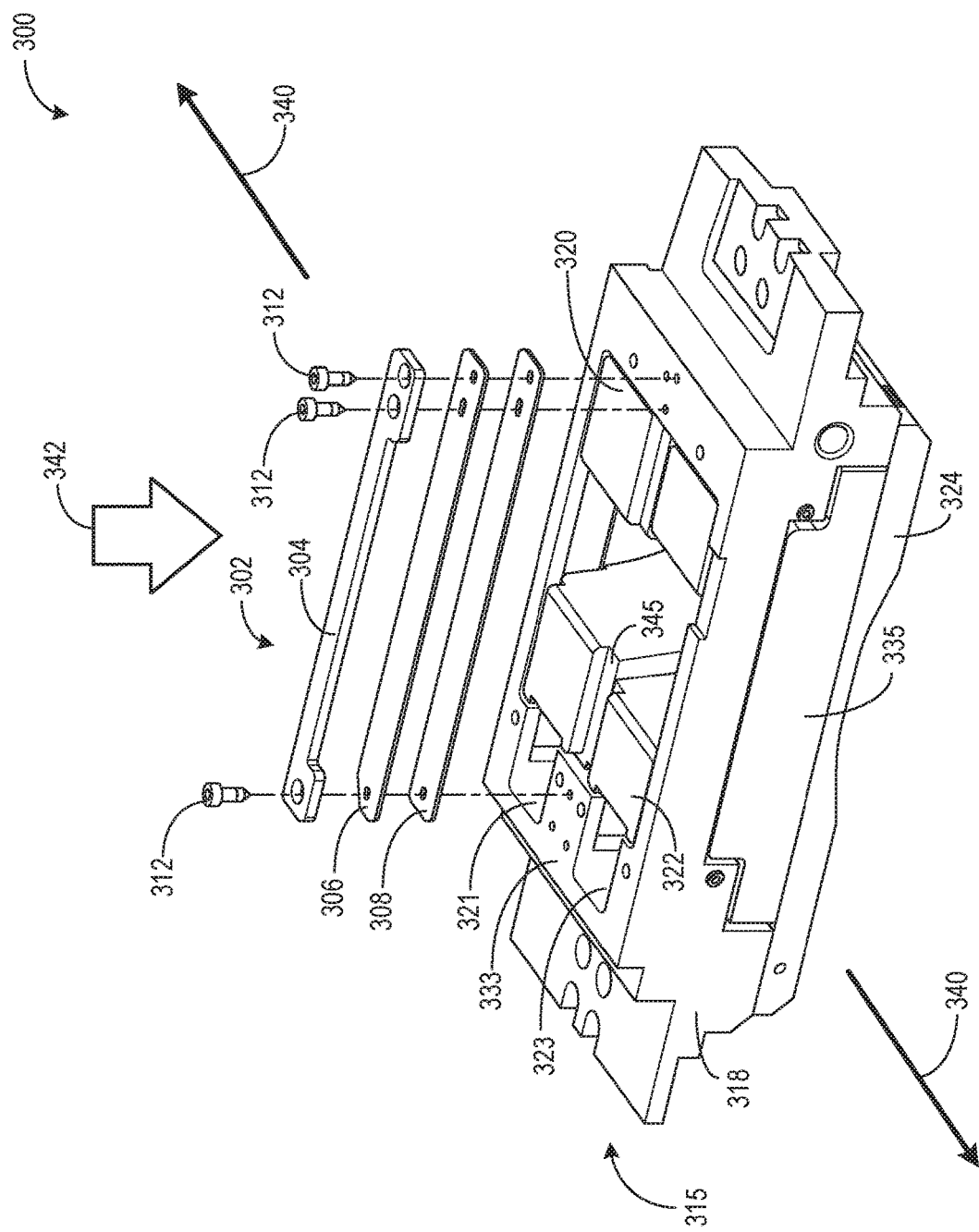
FIG. 3 shows an axonometric view of an example integrated filter assembly including a carriage, a hardening filter, and a plurality of bowtie filters.
Figure 8B:
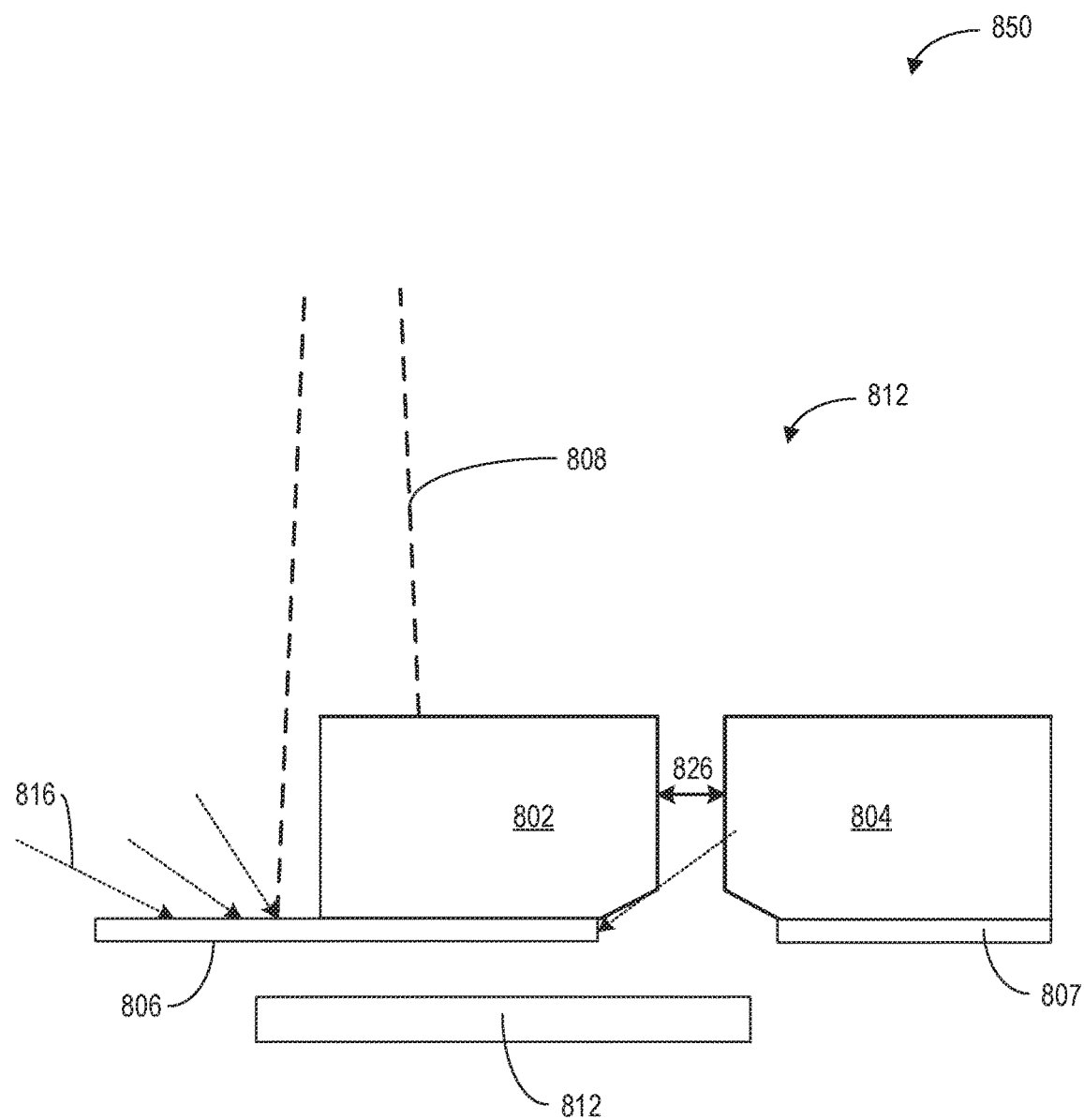
FIG. 8B shows a second position of a collimation arrangement for an x-ray beam including a blocking plate.
Figure 10:
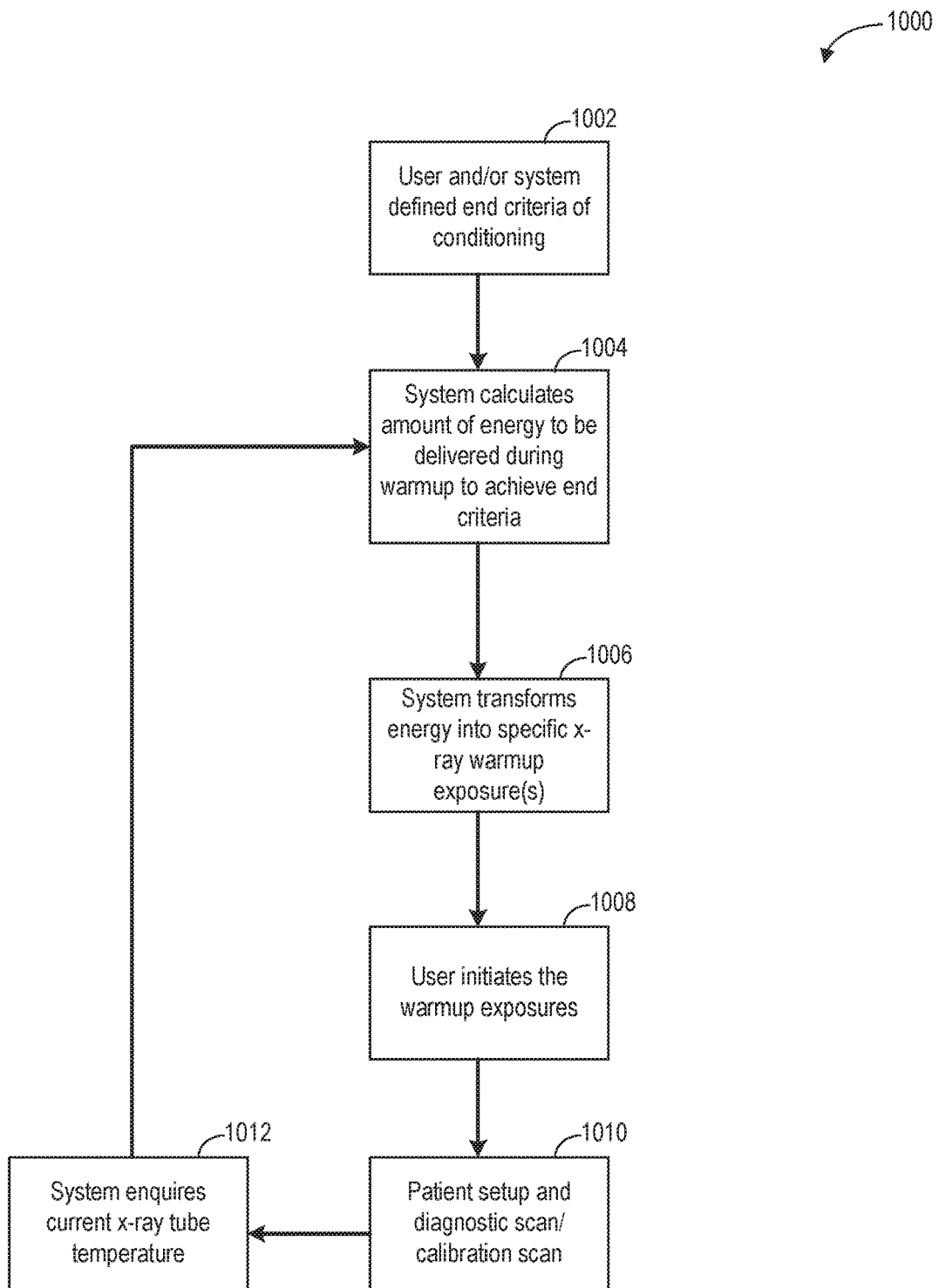
FIG. 10 shows a block diagram illustrating an example open-loop control of x-ray tube temperature prior to a scan.
Figure 11:
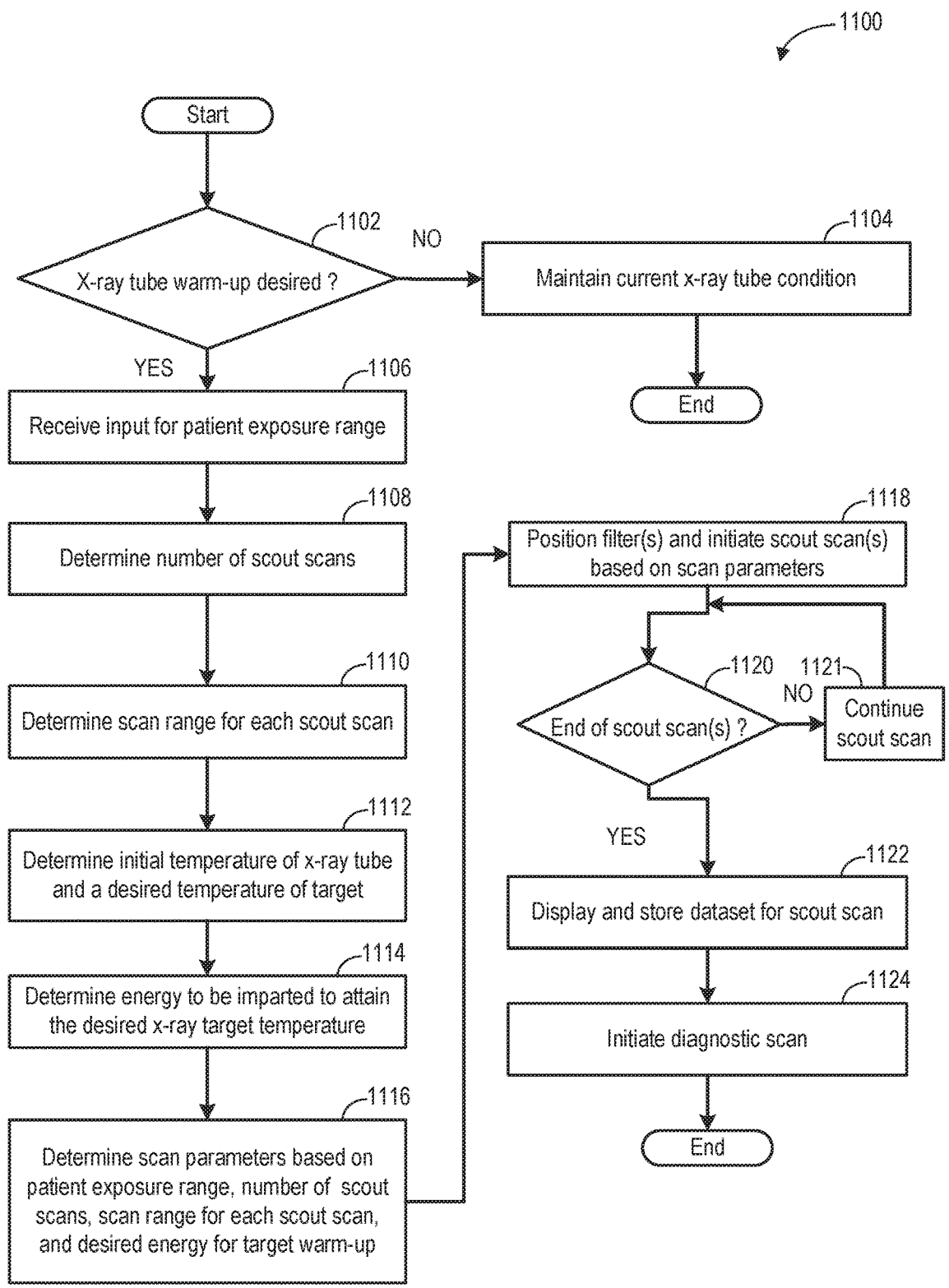
FIG. 11 shows a flow chart of an example method of using a scout scan for x-ray tube conditioning prior to a diagnostic scan.
Figure 12:
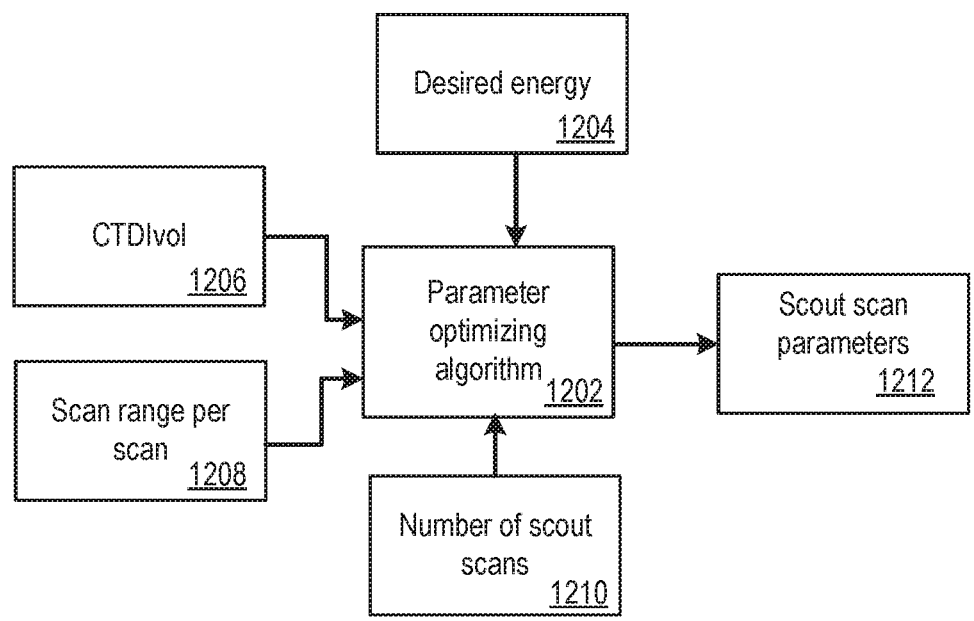
FIG. 12 shows a block diagram illustrating a guided selection of a scout scan protocol.
Figure 13:
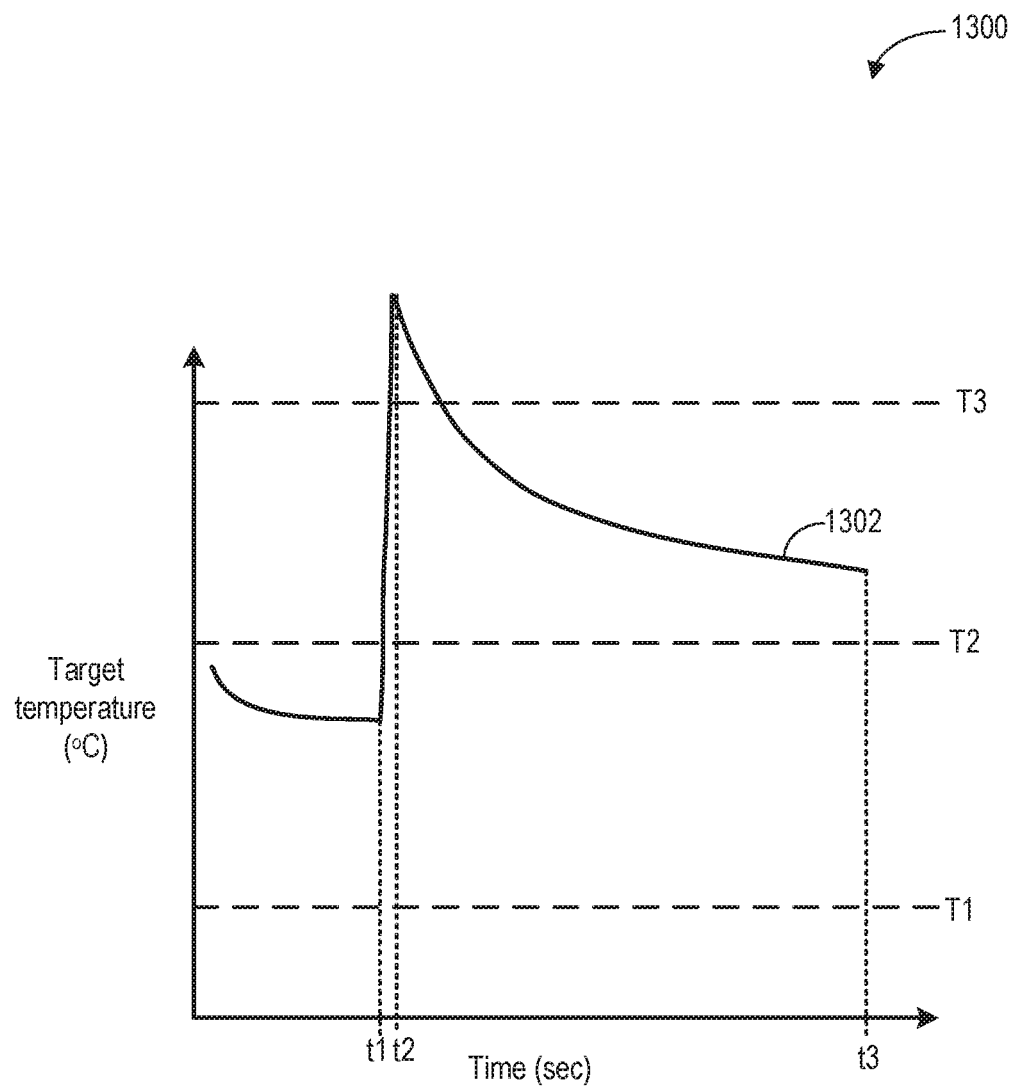
FIG. 13 shows an example plot of variation in x-ray tube temperature during a scout scan and a diagnostic scan.

The following description relates to various embodiments of x-ray imaging of a subject. In particular, systems and methods are provided for CT imaging using one or more of a hardening filter and bowtie filters. FIGS. 1-2 show an example embodiment of an imaging system, wherein the one or more filters are positioned between the radiation source and the imaging subject. Different filters may be selected based on the anatomy of the imaging subject being imaged. FIG. 3 shows an example of an integrated filter assembly including a carriage, a hardening filter, and a plurality of bowtie filters which may be positioned to adjust a spatial distribution and condition the beam reaching the subject. As an example, in a single carriage, two bowtie filters may be positioned next to each other with a hardening filter also coupled to the same carriage between the two bowtie filters. A single bowtie filter or a combination of a hardening filter and a bowtie filter may be positioned in a path of the beam by moving the carriage along an axis perpendicular to the beam. FIGS. 5A-5D show various positions of an example filter assembly with three bowtie filters and a hardening filter. A size of the x-ray beam passing through one or more filters and reaching the subject may be collimated based on a selected aperture size as shown in FIGS. 4A-4E. During conditioning of the x-ray tube prior to a diagnostic scan, a blocking plate, as shown in FIGS. 7 and 8A-8B may be used to block x-ray beam from passing through the collimator and reaching an imaging subject. FIG. 6 shows an example method for imaging a subject using one or more filters included in the integrated filter assembly. Example methods for conditioning an x-ray tube are shown in FIGS. 8 and 11. An example of closed-loop control of x-ray target temperature as part of the x-ray tube conditioning approach is shown in FIG. 10. A block diagram illustrating a guided selection of a scout scan protocol using an algorithm is shown in FIG. 12. An example plot of variation in x-ray tube temperature during a scout scan and a diagnostic scan is shown in FIG. 13.

Though a CT system is described by way of example, it should be understood that the present techniques may also be useful when applied to images acquired using other imaging modalities, such as tomosynthesis, C-arm angiography, and so forth. The present discussion of a CT imaging modality is provided merely as an example of one suitable imaging modality.

Various embodiments may be implemented in connection with different types of imaging systems. For example, various embodiments may be implemented in connection with a CT imaging system in which a radiation source projects a fan- or cone-shaped beam that is collimated to lie within an x-y plane of a Cartesian coordinate system and generally referred to as an "imaging plane." The x-ray beam passes through an imaging subject, such as a patient. The beam, after being attenuated by the imaging subject, impinges upon an array of radiation detectors. The intensity of the attenuated radiation beam received at the detector array is dependent upon the attenuation of an x-ray beam by the imaging subject. Each detector element of the array produces a separate electrical signal that is a measurement of the beam intensity at the detector location. The intensity measurements from all the detectors are acquired separately to produce a transmission profile.

In third-generation CT systems, the radiation source and the detector array are rotated with a gantry within the imaging plane and around an object (such as a region of the subject) to be imaged such that the angle at which the x-ray beam intersects the imaging subject constantly changes. A complete gantry rotation occurs when the gantry concludes one full 360 degree revolution. A group of x-ray attenuation measurements (e.g., projection data) from the detector array at one gantry angle is referred to as a "view." A view is, therefore, each incremental position of the gantry. A "scan" of the object comprises a set of views made at different gantry angles, or view angles, during one revolution of the x-ray source and detector.

In an axial diagnostic scan, the projection data is processed to construct an image that corresponds to a two-dimensional slice taken through the imaging subject. A scout scan (also referred herein as localizer scan) provides a projection view along a longitudinal axis of the imaging subject and generally provides aggregations each including internal structures of the subject. One method for reconstructing an image from a set of projection data is referred to in the art as a filtered backprojection technique. This process converts the attenuation measurements from a scan into integers called "CT numbers" or "Hounsfield units" (HU), which are used to control the brightness of a corresponding pixel on a display.

Beam characteristics such as size, shape, and energy may be different for a scout scan (also referred herein as localizer scan) and a diagnostics scan. During certain scout scans and diagnostic scans, it is desired to use a higher power x-ray source. The higher power improves the quality of the diagnostic scan and increases thermal stability of the x-ray tube including the target. However, an increase in the x-ray power, may increase in x-ray radiation exposure for a patient. The hardening filter may be used in the path of the beam to attenuate the beam and reduce the energy of the x-ray beam prior to it entering the patient's body. The hardening filter along with a bowtie filter may be specifically desired to be used during smaller beams (lower beam coverage) while scans with larger beam coverage may solely use a bowtie filter. The hardening filter and the bowtie filters may be mounted on separate carriages which can be moved in and out of the beam as desired. However, adding multiple carriages will add cost and complexity to the apparatus. Also, the time to complete scans may be longer due to the need to move carriages in and out of the beam between sections of a scan. Therefore, according to embodiments disclosed herein, a single integrated filter assembly may in incorporated including a carriage, a hardening filter, and a plurality of bowtie filters. Based on the scan setup, one or more filters from the carriage may be placed in the path of the beam. By including multiple bowtie and hardening filters in a single integrated filter assembly, reliability of the set up may be increased while cost and complexity of the setup may be decreased.

FIG. 1 illustrates an exemplary CT system 100 configured to allow fast and iterative image reconstruction. Particularly, the CT system 100 is configured to image a subject 112 such as a patient, an inanimate object, one or more manufactured parts, and/or foreign objects such as dental implants, stents, and/or contrast agents present within the body placed on a movable table 228. In one embodiment, the CT system 100 includes a gantry 102, which in turn, may further include at least one x-ray radiation source 104 configured to project a beam of x-ray radiation 106 for use in imaging the subject 112. The x-ray radiation source 104 includes a x-ray tube and a target. The x-ray tube generate x-rays by accelerating and focusing a high-energy beam of electrons onto a rotating target. As individual electrons strike the target, the energy released by interacting with the atoms of the target produces x-ray photons isotropically under a polychromatic spectrum, a maximum energy of the x-ray photons matching that of the incident electrons. The x-ray photons leave the tube through a window that defines an x-ray beam. The beam can then be collimated and conditioned using collimator blades and filter(s).

Specifically, the radiation source 104 is configured to project the x-rays 106 towards a detector array 108 positioned on the opposite side of the gantry 102. Although FIG. 1 depicts only a single radiation source 104, in certain embodiments, multiple radiation sources may be employed to project a plurality of x-rays 106 for acquiring projection data corresponding to the subject 112 at different energy levels. The radiation source may include an x-ray target manufactured of graphite and metal.

In certain embodiments, the CT system 100 further includes an image processing unit 110 configured to reconstruct images of a target volume of the subject 112 using an iterative or analytic image reconstruction method. For example, the image processing unit 110 may use an analytic image reconstruction approach such as filtered backprojection (FBP) to reconstruct images of a target volume of the subject 112. As another example, the image processing unit 110 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the subject 112.

FIG. 2 illustrates an exemplary imaging system 200 similar to the CT system 100 of FIG. 1. In accordance with aspects of the present disclosure, the system 200 is configured to perform automatic exposure control responsive to user input. In one embodiment, the system 200 includes the detector array 108 (see FIG. 1). The detector array 108 further includes a plurality of detector elements 202 that together sense the x-ray beam 106 (see FIG. 1) that pass through a subject 204 such as a patient to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data.

A filter carriage 240 may be mounted within gantry 102 between radiator source 104 and the subject 204. The carriage 240 may travel in and out of the beam in the z-direction while the beam is substantially in the y-direction. Two different bowtie filters, a first bowtie filter 241 and a second bowtie filter 242 are shown in FIG. 2 as an example. The first bowtie filter 241 is housed within a first slot formed in a cavity of the carriage and wherein the second bowtie filter 242 is housed within a second slot formed in the cavity of the carriage, the first slot separated from the second slot via a tab. The bowtie filters are shown here in rectangular shape as an example. Each and every bowtie filter is rigid and non-deformable. The bowtie filters may alternatively have different shapes and material constructions to provide proper x-ray special spectrum for imaging various types of anatomies. A hardening filter 243 is shown coupled to the carriage 240 between the two bowtie filters 241 and 242. The hardening filter 243 may at least partially overlap with each of the first bowtie filter 241 and the second bowtie filter 242. In one example, the hardening filter only partially overlaps with each of the first bowtie filter 241 and the second bowtie filter 242. In another example, the hardening filter 243 may completely overlap with one of the first bowtie filter 241 and the second bowtie filter 242. The hardening filter 243 includes each of a rectangular support structure, and one or more rectangular metallic sheets stacked under the support structure. The rectangular support structure may be made of aluminum and the one or more rectangular metallic sheets may be made of copper with each of the one or more rectangular metallic sheets having a different thickness. An example of a carriage including a plurality of filters is shown in FIG. 3.

In this example, the x-ray beam 106 passes through the hardening filter 243 and the second bowtie filter 242. However, the carriage 240 may be moved to a position such that the beam may pass through a bowtie filter (first or second) and not through the hardening filter. As an example, if the carriage 240 is moved further towards the left, the beam may solely pass through the second bowtie filter 243. In this way, it is possible to pass the beam through a bowtie filter and each of a hardening filter and a bowtie filter.

The bowtie filter may change the spatial distribution of the radiation beam in the axial plane of the imaging subject (such as a patient). For example, the re-distributed radiation beam may have higher energy at the center and lower energy at the periphery of the subject. Each of the bowtie filters may be designed to image a specific anatomy or section of the human body, such as head, chest, and abdomen. During imaging, one of the bowtie filters may be selected based on the anatomy of the subject to be scanned, and the selected filter may be placed into the radiation beam path. Responsive to a change in the anatomy, the filter may be changed from one to another. Based on a nature of the scan, the carriage may be positioned such that the hardening filter may or may not be placed in the radiation beam path. The hardening filter may attenuate the beam and remove low energy components thereby conditioning the beam for specific scans such as a scout scan. Example arrangement of the filters in the filter housing is shown in FIGS. 5A-5D.

A filter driving system, such as the filter driving system 590 shown in FIG. 5, may be coupled to the carriage 240 to move the one or more filters into and out of the radiation beam path. In one embodiment, a motor may couple the filters in the carriage through a shaft. The bowtie filters may be switched from one to another and/or a hardening filter may be introduced or removed from the beam path by translating the filters along the shaft by rotating the shaft with a motor. One of the filters may be selected and translated into the x-ray beam between the radiation source and the imaging subject to image a specific section of the human body. Computing device 216 may send command to the motor of the filter driving system to move the selected filter in to the radiation beam. The filter driving system may also send filter position information back to the computing device 216.

In certain embodiments, the system 200 is configured to traverse different angular positions around the subject 204 for acquiring desired projection data. Accordingly, the gantry 102 and the components mounted thereon (such as the radiation source 104, the filter housing 240, and the detector 202) may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

In one embodiment, the system 200 includes a control mechanism 208 to control movement of the components such as rotation of the gantry 102 and the operation of the x-ray radiation source 104. In certain embodiments, the control mechanism 208 further includes an x-ray controller 210 configured to provide power and timing signals to the radiation source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The data sampled and digitized by the DAS 214 is transmitted to a computing device (also referred to as processor) 216. In one example, the computing device 216 stores the data in a storage device 218. The storage device 218, for example, may include a hard disk drive, a floppy disk drive, a compact disk-read/write (CD-R/W) drive, a Digital Versatile Disc (DVD) drive, a flash drive, and/or a solid-state storage device.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard or a touchscreen to allow the operator to specify the commands and/or scanning parameters.

Although FIG. 2 illustrates only one operator console 220, more than one operator console may be coupled to the system 200, for example, for inputting or outputting system parameters, requesting examinations, and/or viewing images. Further, in certain embodiments, the system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks.

In one embodiment, for example, the system 200 either includes, or is coupled to a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a motorized table 228. Particularly, the table motor controller 226 moves the table 228 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the system 200 and instead the computing device 216 may perform one or more functions of the image reconstructor 230. Moreover, the image reconstructor 230 may be located locally or remotely, and the image reconstructor 230 may be operatively connected to the system 100 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 transmits the reconstructed images to the computing device 216 for generating useful patient information for diagnosis and evaluation. In certain embodiments, the computing device 216 transmits the reconstructed images and/or the patient information to a display 232 communicatively coupled to the computing device 216 and/or the image reconstructor 230.

FIG. 3 shows an axonometric view 300 of an example integrated filter assembly 315. The filter assembly 315 may include a rectangular carriage 318. In one example, carriage 318 may be the carriage 240 in FIG. 2. The carriage 318 may include a first slot 321 and a second slot 323 formed length-wise within a cavity of the carriage 318. The first slot 321 may be separated from the second slot 323 via a tab 333. In one example, each of the two slots 321 and 323 may extend through the entire length of the carriage 318. In another example, each of the two slots 321 and 323 may partially extend through the length of the carriage 318.

A first bowtie filter 320 may be housed within the first lot 321 while a second bowtie filter 322 may be housed in the second slot 323. In one example, the first bowtie filter 320 and the second bowtie filter 322 may be positioned next to each other but not in contact. In another example, the first bowtie filter 320 and the second bowtie filter 322 may be positioned next to each other in face-sharing contact. Each of the first bowtie filter 320 and the second bowtie filter 322 may be shaped as a "bowtie" with a first, straight long side and a second, parallel long side including a central ridge. In one example, the first bowtie filter 320 and the second bowtie filter 322 may be of the same size (such as width, length, thickness, etc.) In another example, the first bowtie filter 320 and the second bowtie filter 322 may be of different sizes (such as width, length, thickness). Each of the first bowtie filter 320 and the second bowtie-filter 322 may be formed of graphite. A bowtie filter may be used to adjust spatial distribution of an x-ray beam 342 passing through the filter and the size of a bowtie filter governs a level of spatial distribution adjustments made to the x-ray beam 342 passing through the filter. The carriage 318 may include cut-outs 335 on side wall through which a bowtie filter may be visible. As shown in this example, the second bowtie filter 322 may be co-planer with a side wall and cut-out 335 of the carriage 318. The bowtie filters may be secured inside their respective slots via nuts and bolts.

A hardening filter 302 may be coupled to the carriage 318 between the first bowtie filter 320 and the second bowtie filter 322. The hardening filter 302 may be embedded in a recess 345 between the first bowtie filter 320 and the second bowtie filter 322. The length of the hardening filter 302 may be higher than or equal to the length of each of the first bowtie filter 320 and the second bowtie filter 322. However, the width of the hardening filter 302 may be narrower than the width of each of the first bowtie filter 320 and the second bowtie filter 322. As the rectangular hardening filter 302 is positioned between the first bowtie filter 320 and the second bowtie filter 322, the hardening filter 302 may at least partly overlap with each of the first bowtie filter 320 and the second bowtie filter 322 and may be in face sharing contact with the top/side surfaces of the bowtie filters.

The hardening filter 302 may include a support structure 304, and one or more metallic sheets underneath the support structure 304. In this example, a first metallic sheet 306 and a second metallic sheet 308 may be positioned under the support structure 304. Each of the first metallic sheet 306, the second metallic sheet 308, and the support structure 304 may be stacked together and bolted at each end to the carriage 318 via a plurality of bolts 312. In this example, a plurality of concentric holes are formed on two ends of each of the first metallic sheet 306, the second metallic sheet 308, and the support structure 304 and each bolt (used to attach the layers of the hardening filter 304 to the carriage 318) may pass through each of the concentric holes present in each layer. As an example, one end of the hardening filter 302 may be attached to the tab 333 of the carriage 318. In one example, the support structure 304 may be made of a metal such as aluminum, and first metallic sheet 306 and the second metallic sheet 308 may be made of a same metal or different metals. Copper may be used to form one or both of the first metallic sheet 306 and the second metallic sheet 308.

The hardening filter 302 may be used to intercept lower energy radiation, thereby attenuating and "hardening" the x-ray beam 342 passing through the hardening filter 302. The degree of beam attenuation may depend on one or more of a number of attenuation layers (such as metallic sheets), the thickness of each attenuation layer, the materials used in the attenuation layers, and the overall size of the attenuation layers.

As an example, when using thinner or weaker sheets of hardening material in 302, the support plate 304 may be used to limit deflection of 302 due to gantry rotational forces which may act to bend the middle of the hardening material. In this embodiment, the support plate is positioned outside of the cross-sectional area of the hardened x-ray beam that is used for imaging. In this way, the hardening filter may be solely accounted for in hardening the imaging x-ray beam while being mechanically strengthened by the support plate proximal to the area where the imaging beam passes through the hardening filter. Furthermore, the support plate may be made from a stiff but lightweight material such as aluminum to minimize excess x-ray scatter near the hardening filter.

An aluminum filter 324 may be coupled to the underside of the carriage 318 and may extend along the entire lower surface of the carriage 318. The aluminum filter may further condition the x-ray beam 342 after the beam has passed through one or more of the hardening filter and bowtie filters.

During an imaging, an x-ray beam 342 may first pass through the hardening filter 302 followed by a bowtie filter and then the aluminum filter 324. The carriage 318 may be moved along a direction perpendicular to that of the beam 342, as shown by arrows 340 to position the beam on a bowtie filter and the hardening filter 302. A level of beam attenuation and spatial distribution may be adjusted by selecting a combination of hardening filter 302 and bowtie filters. In one example, the carriage may be positioned such that the beam passes through the hardening filter 302 and the first bowtie filter 320, the beam proximal to an edge of the first bowtie filter overlapping with the hardening filter 302. In another example, the carriage may be positioned such that the beam passes the first bowtie filter 320 only, the beam proximal to another edge of the first bowtie filter not overlapping with the hardening filter 302. In yet another example, the carriage may be positioned such that the beam passes through the hardening filter 302 and the second bowtie filter 322, the beam proximal to an edge of the second bowtie filter 322 overlapping with the hardening filter 302. In a further example, the carriage may be positioned such that the beam passes the second bowtie filter 322 only, the beam proximal to another edge of the second bowtie filter not overlapping with the hardening filter 302. After passing through one or more of the hardening filter 302 and the bowtie filters, the beam may always pass through the aluminum filter 324 before entering a subject that is scanned.

Attenuation of the beam via a hardening filter may be specifically desired during a scout scan which may precede a diagnostic scan. During a diagnostic scan, a bowtie filter without the hardening filter may be used for diagnostic scans. Typically, for a scout scan a smaller beam (coverage) may be used relative to the beam size used for diagnostic scans. The smaller beam may completely pass through the hardening filter 302 which is narrower than a bowtie filter. By incorporating the hardening filter with the bowtie filter, a single carriage may be used for both scout scans and diagnostic scans, thereby reducing the number of components and the time needed to switch between carriages during a scout scan and a successive diagnostic scan. Also, by using a hardening filter, a higher power x-ray source with increased x-ray tube temperature may be used during a scan without increasing radiation exposure of the subject. The higher power may improve the quality of the scout scan and/or subsequent diagnostic scans and improve thermal stability of the x-ray tube including the target. The consistently higher temperature of the x-ray tube target may contribute to long-term reliability of the device as it remains closer to an optimal operating temperature; fewer temperature cycles of the internal parts contribute to better reliability.

In this way, FIGS. 1-3 provide for an imaging system, comprising: a gantry for receiving an imaging subject, a radiation source positioned in the gantry for emitting radiation exposure, a detector positioned on the opposite of the gantry relative to the radiation source, a motorized table for moving the imaging subject within the gantry, a computation device with instructions stored in a non-transient memory, a filter carriage mounted to the gantry, a first bowtie filter, a second bowtie filter, and a hardening filter positioned in the filter carriage, the hardening filter mounted in between the first bowtie filter and the second bowtie filter and partially overlapping with each of the first bowtie filter and the second bowtie filter, and a filter driving system for switching filters by moving one or more of the first bowtie filter, the second bowtie filter, and the hardening filter into or out of the radiation beam.

FIGS. 4A-4E show a cross-section of collimation arrangement 412 for an x-ray beam. The collimation arrangement 412 may include the integrated filter assembly 315 of FIG. 3. The integrated filter assembly 315 may include a hardening filter 302, a first bowtie filter 320, a second bowtie filter 322, and an aluminum filter 324. An x-ray beam may pass through a gap (aperture) formed between a first collimator blade 408 and a second collimator blade 410 after passing through the integrated filter assembly 315. Each of the first collimator blade 408 and the second collimator blade 410 may be formed from lead or another attenuating material like tungsten which may adsorb any radiation it encounters. After passing through the gap between the first collimator blade 408 and the second collimator blade 410, the x-ray beam may exit the collimation arrangement 412 (a collimator) via a collimator output port (opening) 418. The gap between the first collimator blade 408 and the second collimator blade 410 may correspond to the desired beam coverage. A beam of different sizes may be adjusted based on the scan desired and characteristic of the subject (such as the anatomy to be scanned). As such, a size of beam used in a scout scan may be smaller than a size of beam used for a diagnostic scan of a specific anatomy. In the example embodiments of FIGS. 4A-4E, specific beam widths of 5 mm, 10 mm, 15 mm, 20 mm, and 25 mm are shown, however beams of other widths may be used in other embodiments.

In the first embodiment 400 of the collimation arrangement 412, the desired x-ray beam size is 5 mm. The carriage 302 is positioned in a way that the x-ray beam 415 passes through each of hardening filter 302, the first bowtie filter 320, and the aluminum filter. After exiting the integrated filter assembly 315, the x-ray beam 415 is collimated to a size of 5 mm as it then passes through an aperture 414 between first collimator blade 408 and a second collimator blade 410. By adjusting the relative positioning of the first collimator blade 408 and the second collimator blade 410, the size of the aperture 414 may be adapted to 5 mm. After passing through the integrated filter assembly 315 wherein the x-ray beam is conditioned as the beam passes through the filters, the beam is collimated to the desired size of 5 mm via the aperture 414. The x-ray beam 415 exiting the aperture 414 may then reach the subject to be scanned.

In the second embodiment 420 of the collimation arrangement 412, the desired x-ray beam size is 10 mm. The carriage 302 is positioned in a way that allows the x-ray beam 425 to pass through each of hardening filter 302, the first bowtie filter 320, and the aluminum filter. After exiting the integrated filter assembly 315, the x-ray beam 425 is collimated to a size of 10 mm as it then passes through an aperture 424 between first collimator blade 408 and a second collimator blade 410. By adjusting the relative positioning of the first collimator blade 408 and the second collimator blade 410, the size of the aperture 424 may be adapted to 10 mm. After passing through the integrated filter assembly 315 wherein the x-ray beam 425 is conditioned as the beam passes through the filters, the beam is collimated to the desired size of 10 mm via the aperture 424. The x-ray beam 425 exiting the aperture 424 may then reach the subject to be scanned.

In the third embodiment 440 of the collimation arrangement 412, the desired x-ray beam size is 15 mm. The carriage 302 is positioned in a way that the x-ray beam 445 passes through each of hardening filter 302, the first bowtie filter 320, and the aluminum filter. After exiting the integrated filter assembly 315, the x-ray beam 445 is collimated to a size of 15 mm as it then passes through an aperture 444 between first collimator blade 408 and a second collimator blade 410. By adjusting the relative positioning of the first collimator blade 408 and the second collimator blade 410, the size of the aperture 444 may be adapted to 15 mm. After passing through the integrated filter assembly 315 wherein the x-ray beam is conditioned as the beam passes through the filters, the beam is collimated to the desired size of 15 mm via the aperture 444. The x-ray beam 445 exiting the aperture 444 may then reach the subject to be scanned.

In the fourth embodiment 460 of the collimation arrangement 412, the desired x-ray beam size is 20 mm. The carriage 302 is positioned in a way that the x-ray beam 465 passes through each of hardening filter 302, the first bowtie filter 320, and the aluminum filter. After exiting the integrated filter assembly 315, the x-ray beam 465 is collimated to a size of 20 mm as it then passes through an aperture 464 between first collimator blade 408 and a second collimator blade 410. By adjusting the relative positioning of the first collimator blade 408 and the second collimator blade 410, the size of the aperture 464 may be adapted to 20 mm. After passing through the integrated filter assembly 315 wherein the x-ray beam is conditioned as the beam passes through the filters, the beam is collimated to the desired size of 20 mm via the aperture 464. The x-ray beam exiting the aperture 464 may then reach the subject to be scanned.

In the fifth embodiment 480 of the collimation arrangement 412, the desired x-ray beam size is 25 mm. The carriage 302 is positioned in a way that the x-ray beam 485 passes through each of hardening filter 302, the first bowtie filter 320, and the aluminum filter. After exiting the integrated filter assembly 315, the x-ray beam 485 is collimated to a size of 25 mm as it then passes through an aperture 484 between first collimator blade 408 and a second collimator blade 410. By adjusting the relative positioning of the first collimator blade 408 and the second collimator blade 410, the size of the aperture 484 may be adapted to 25 mm. After passing through the integrated filter assembly 315 wherein the x-ray beam is conditioned as the beam passes through the filters, the beam is collimated to the desired size of 25 mm via the aperture 484. The x-ray beam exiting the aperture 484 may then reach the subject to be scanned.

FIGS. 5A-5D show an example configuration of a filter assembly 500 with three filters 505, 506, and 507 within filter housing 510. As an example, each of the three filters 505, 506, and 507 may be bowtie filters. In this example, the first filter 508 and the second filter 506 are positioned together in a carriage 504. A hardening filter 513 may be coupled to the carriage 504 between the first filter 508 and the second filter 506. In one example, the carriage 504 may be the carriage 318 in FIG. 3.

The carriage 504 may be coupled to a ballscrew 511, and the carriage may be translated along a first shaft 505 by rotating the first shaft with a first motor 502. The third filter 507 may be coupled to a ballscrew 512 and may be translated along a second shaft 509 by rotating the second shaft with a second motor 503. A localized clearance feature (not shown) is present in carriage 504 to avert interference of the second shaft 509 with the carriage 504 as the carriage 504 translates along the first shaft 505. The direction of the x-ray beam (such as x-ray radiation 106 of FIGS. 1-2) is indicated by 501. One of the three filters along with the hardening filter 513 may be selectively translated into the beam path of the x-ray beam by rotating one or both shafts 505 and 509 via motors 502 and 503, respectively. The first and the second shafts may be aligned in one line, and are spaced apart from each other by a gap 523. The x-ray beam 501 may transmit through the gap 523. The motor (such as motor 503), the shaft (such as shaft 509) coupled to the motor, and the filter (such as filter 507) coupled to the shaft may form a filter driving system 590. The filter assembly 500 may include one or more filter driving systems.

Figure 5A:
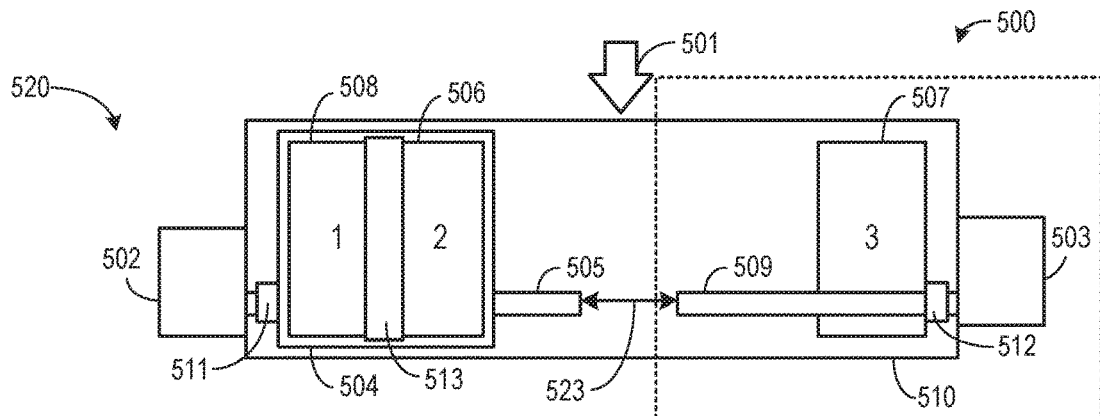
FIG. 5A shows a first position of a filter assembly with three bowtie filters and a hardening filter.
Figure 6:
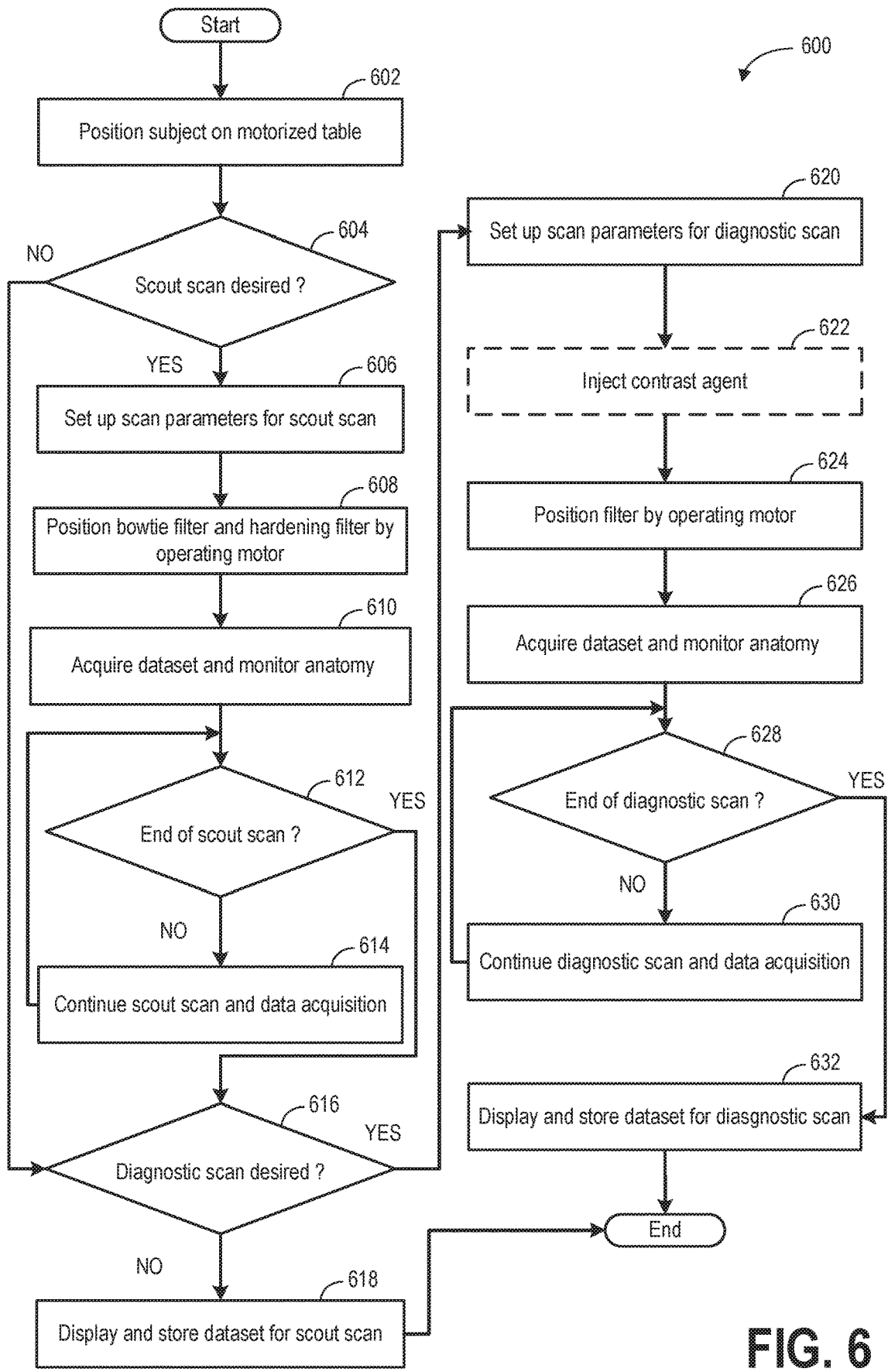
FIG. 6 shows a flow chart of an example method for imaging using multiple filters included in the integrated filter assembly.

FIG. 5A shows a first position 520 of the filter assembly 500. The x-ray beam 501 transmits through the filter housing 510 without passing through any filter. The carriage 504 including the first filter 508, the second filter 506, and the hardening filter 513 may be located closer to the first motor 502, and the third filter may be located closer to the second motor 503.

Figure 5B:
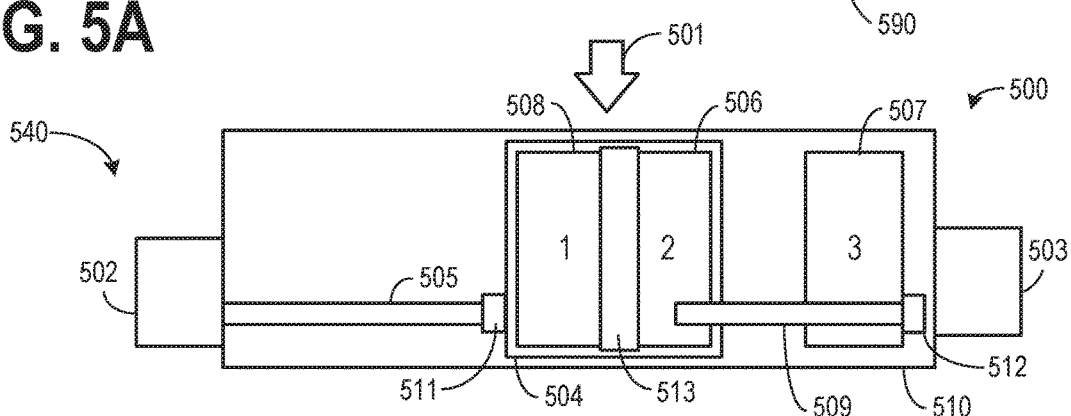
FIG. 5B shows a second position of the filter assembly of FIG. 5A.

FIG. 5B shows a second position 540 of the filter assembly 500. The x-ray beam 501 transmits though each of the hardening filter 513 and the first filter 508 in the filter housing 810. The filter assembly 500 may transit from the first position 520 to the second position 540 by actuating the first motor 502 and translating the hardening filter 513 and the first filter 508 (in carriage 504) into the x-ray beam path.

Figure 5C:
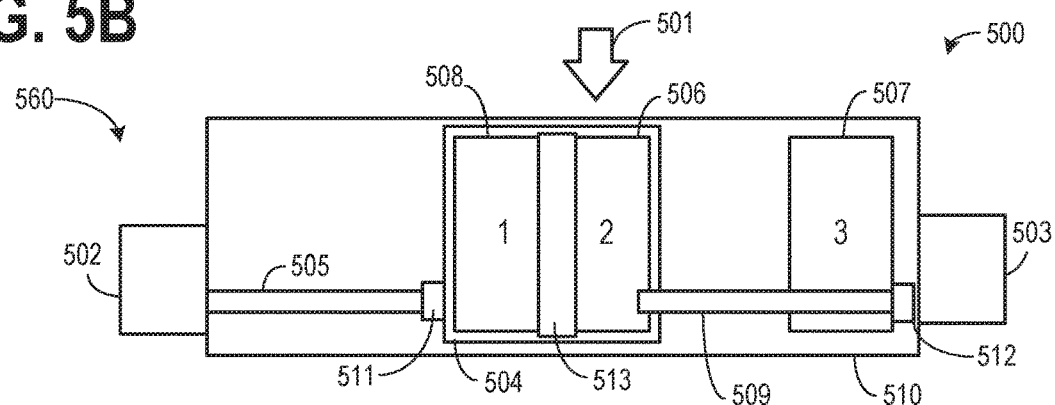
FIG. 5C shows a third position of the filter assembly of FIG. 5A.

FIG. 5C shows a third position 560 of the filter assembly 500. The x-ray beam 501 solely transmits though the second filter 506 (without the hardening filter 513 in between) in the filter housing 810. The filter assembly 500 may transit from the first position 520 or the second position 540 to the third position 560 by actuating the first motor 502 and translating the second filter 506 (in carriage 504) into the x-ray beam path.

Figure 5D:
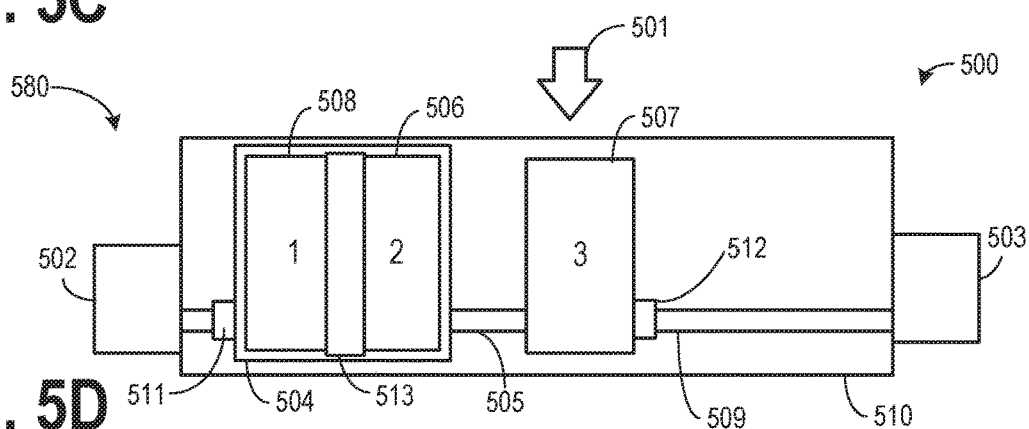
FIG. 5D shows a fourth position of the filter assembly of FIG. 5A.

FIG. 5D shows a fourth position 580 of the filter assembly 500. The x-ray beam 501 transmits through the third filter 507 in the filter housing 510. The filter assembly 500 may transit from any of the above-mentioned first, second, or third position to the fourth position 580 by actuating the first motor 502 to translate the carriage 504 closer to the first motor 502, and subsequently or simultaneously actuating the second motor 503 to translate the third filter 507 into the x-ray beam path.

Based on the instructions stored in the non-transient memory, the computing device (such as computing device 216 of FIG. 2) may move the filter assembly from any one of the above positions to another position by actuating one or more of the two motors. In one embodiment, two filters and a hardening filter are positioned in a carriage. As one example, the two filters may be coupled to one shaft and driven by one motor. As another example, one of the two filters and the hardening filter are coupled to one shaft and driven by one motor, and the other of the two filters is coupled to a second shaft and driven by a second motor. In another embodiment, more than three filters and multiple hardening filters may be arranged within the filter housing. For example, the numbers of filters coupled to each shaft are the same, if the total number of filters in the housing is even. The numbers of filters coupled to each shaft is different, if the total number of filters in the housing is odd.

In yet another embodiment, the arrangement of the filters in the filter housing may be based on the type of the filters. Herein, the filter type may be determined by the section of the subject that the filter is designed to image. For example, the first filter used for imaging the first section of the subject and the second filter used or imaging the second section of the subject may be positioned next to each other, if the first section and the second section are connected. The first filter and the second filter may be positioned apart from each other (such as separated by another filter), if the first section and the second section are not connected. As an example, the filter for imaging the abdomen maybe positioned next to the filter for imaging the chest, but apart from the filter for imaging the head. In this way, when the chest is imaged after imaging the abdomen, the filters may be quickly switched from one to another. When the head is imaged after imaging the abdomen, the duration for filter switching may be longer, as the imaging subject needs to be physically moved from imaging the abdomen to imaging the head. The hardening filter may be coupled between two filters which may be used for a scout scan.

In other embodiments, a carriage including filters may be translated with any one of a rack and pinion, a belt, or a cable-driven system. A filter driving system in the filter assembly may switch one filter to another within two seconds. For example, the filter can be translated 3-5 inches in less than two seconds by the filter driving system.

FIG. 6 shows an example method 600 for performing image scans using multiple filters included in an integrated filter assembly (such as integrated filter assembly 325 in FIG. 3). Method 600 achieves image acquisition of multiple anatomies of the imaging subject by changing filters within a same carriage between successive scans. Method 600 and all methods described herein may be performed according to instructions stored in the non-transitory memory in a computing device (such as computer 216 of FIG. 2) of the imaging system.

At 602, a subject (such as subject 204 in FIG. 2) of the imaging scans may be positioned on a motorized table (such as table 228 in FIG. 2). A table motor controller may move the table so that a proper section of the subject is within the gantry for imaging.

At 604, the routine includes determining if a scout scan is desired. A scout scan provides a projection view along a longitudinal axis of the imaging subject and generally provides aggregations each including internal structures of the subject. During a scout scan, while all the components of the imaging system may be maintained in a stationary position, the subject may be passed through the imaging system to perform a scan on the subject. A scout scan may be used to identify a region of interest of the subject for a subsequent diagnostic scan.

If it is determined that a scout scan is desired, at 606, scan parameters may be set up for carrying out a scout scan. For example, a user may input or select the scan parameters according to a scanning protocol or a menu. The scan parameters may include the type and sequence of the filters that are going to be used during the scan. As an example, for a scout scan a bowtie filter along with a hardening filter may be used for conditioning the x-ray beam used for imaging the subject. Scan parameters may also include setting scan timing. As one example, the scan timing may include a start time and a duration for imaging each section.

At 608, a bowtie filter and a hardening filter may be positioned in the path of the x-ray beam by operating a motor coupled to a carriage including the bowtie filter (such as bowtie filter 320 in FIG. 3) and the hardening filter (such as hardening filter 302 in FIG. 3). The carriage may be moved along a shaft in a plane perpendicular to the plane of the x-ray beam to position the bowtie filter and the hardening filter in the beam. The controller may actuate the motor to move the shaft and the carriage to the desired position. The bowtie filter may change the spatial distribution of the radiation beam in the axial plane of the imaging subject (such as a patient). For example, the re-distributed radiation beam may have higher energy at the center and lower energy at the periphery of the subject. A hardening filter may intercept lower energy radiations, thereby attenuating and "hardening" the beam. The hardening filter may at least partially overlap with the bowtie filter and the beam may first pass through the hardening filter and then enter the bowtie filter.

At 610, method 600 may start acquiring the dataset of the imaging subject and simultaneously monitor the anatomy of the imaging subject. For example, the radiation source (such as 104 of FIGS. 1-2) may be activated, and radiation exposure (such as 106 of FIGS. 1-2) of the imaging subject through the bowtie filter and the hardening filter may be started. For a scout scan, a smallest permissible beam may be used. In one example, the beam may be 5 mm. By using a hardening filter to attenuate the beam reaching the subject, a higher power x-ray source with increased x-ray tube temperature may be used during the scout scan without increasing radiation exposure of the subject. The higher power improves the quality of the diagnostic scan and improves thermal stability of the x-ray tube including the target. In one example, a 50 kW x-ray power scan technique (100 kV, 500 mA) may be used.

The dataset is acquired from the detector (such as 108 of FIG. 2) upon receiving the transmitted radiation signal from the imaging subject. As one example, the anatomy of the imaging subject may be monitored by analyzing the acquired dataset. As another example, the anatomy of the imaging subject may be estimated by the currently imaged location. The currently imaged location may be calculated based on the starting location of the scan and the travel distance of the motorized table. In one embodiment, the anatomies of the subject may be grouped in different types. For example, the anatomy of a human body may be grouped based on size, type such as the head, the chest, and the abdomen.

At 612, the routine includes determining if the scout scan has ended. The end of the scout scan may be determined based on the protocol setup at step 606. If it is determined that the scout scan has not ended, at 614, the scout scan may be continued, and data may be acquired.

If it is determined that the scout scan has ended, at 616, the routine includes determining if a diagnostic scan may is desired. As an example, a decision to carry out the diagnostic scan may be made based on the images reconstructed from the data acquired during the scout scan. The image from the scout scan may be two-dimensional or three-dimensional. Based on the scout scan, a specific anatomy may be selected for a diagnostic scan. The diagnostic scan may provide a detailed image of the specific anatomy which might not be available via the scout scan.

If at 604, it is determined that a scout scan is not desired, the routine may directly proceed to step 616 for determining if a diagnostic scan is desired. A scout scan may not always precede a diagnostic scan.

If it is determined that a diagnostic scan is not desired and a scout scan has been completed, at 618, the acquired dataset from the scout scan is displayed and stored. In one embodiment, dataset acquired from different sections of the subject may be re-constructed to form an image. The acquired dataset, as well as the processed images may be saved in the storage of the imaging system and no further scans may be carried out. The routine may then end.

If it is determined that a diagnostic scan is desired, the routine may proceed to step 620 wherein the scan parameters may be set up for carrying out a diagnostic scan. A user may input or select the scan parameters according to a scanning protocol or a menu. The scan parameters may include the type and sequence of the filters that are going to be used during the scan. The type of the filters may be chosen based on the anatomy of imaging subject that is to be imaged. The parameters may also include setting scan timing. As one example, the scan timing may include a start time and a duration for imaging each section. Anatomy information of the imaging subject may be loaded to the memory of the computation device. The anatomy information may be acquired from a pre-scan. The anatomy information may be acquired from the prior scout scan or a localized scan. This step may also include moving the imaging subject via the motorized table so that the proper section of the subject is within the gantry for imaging.

At 622, a contrast agent may be injected into the imaging subject. The contrast agent may enhance the contrast of images captured specifically for certain anatomies. This step is optional and the diagnostic scan may be carried out without use of a contrast agent.

At 624, a bowtie filter may be positioned in the path of the x-ray beam by operating a motor coupled to a carriage including the bowtie filter. The type of the filter may be determined based on the anatomy of the currently imaged section of the subject. The carriage may be moved along a shaft in a plane perpendicular to the plane of the x-ray beam to position the bowtie filter in the beam. For a diagnostic scan, a larger beam size is used and therefore a hardening filter may no longer be used. In one example, the bowtie filter used for the diagnostic scan may be same as the bowtie filter used in the scout scan. In another example, the bowtie filter used for the diagnostic scan may be different from the bowtie filter used in the scout scan. In this way, a single carriage including one or more bowtie filters and a hardening filter may be used for both the scout scan and the diagnostic scan without the need for additional components.

At 626, dataset of the imaging subject may be acquired and simultaneously the anatomy of the imaging subject may be monitored. For example, the radiation source may be activated, and radiation exposure of the imaging subject through the selected bowtie filter may be started. For a diagnostic scan, a beam size of 25 mm-160 mm may be used. The dataset is acquired from the detector upon receiving the transmitted radiation signal from the imaging subject. As one example, the anatomy of the imaging subject may be monitored by analyzing the acquired dataset. As another example, the anatomy of the imaging subject may be estimated by the currently imaged location. The currently imaged location may be calculated based on the starting location of the scan and the travel distance of the motorized table. In one embodiment, the anatomies of the subject may be grouped in different types. For example, the anatomy of a human body may be grouped based on size, types of such as the head, the chest, and the abdomen.

At 628, the routine includes determining if the diagnostic scan has ended. The end of the diagnostic scan may be determined based on the protocol setup at step 620. If it is determined that the diagnostic scan has not ended, a 630, the diagnostic scan may be continued and data may be acquired.

If it is determined that the diagnostic scan has ended, the acquired dataset from the diagnostic scan is displayed and stored. In one embodiment, dataset acquired from different sections of the subject may be re-constructed to form an image. The acquired dataset, as well as the processed images may be saved in the storage of the imaging system and no further scans may be carried out. The routine may then end.

In this way, during a first imaging (such as a scout scan), a carriage may be moved to position a hardening filter and a first bowtie filter housed in the carriage in a path of a radiation beam between a radiation source and an imaging subject and during a second imaging (such as a diagnostic scan), the carriage may be moved to move the hardening filter and the first bowtie filter out of the path of the radiation and then position a second bowtie filter housed in the carriage in the path of the radiation.

In this way, a single carriage may include one or more bowtie filter and hardening filters which may be selectively positioned in a path of an x-ray beam entering a subject without having to stack multiple carriages and switch carriages between scans. The technical effect of attenuating a beam reaching the subject by using a hardening filter is that a higher powered x-ray source with increased x-ray tube temperature may be used during a scan without increasing radiation exposure of the subject. Overall the higher power improves the quality of the diagnostic scan and improves thermal stability of the x-ray tube including the target.

Prior to an x-ray exposure for a diagnostic scan of the imaging subject, the temperature of the x-ray tube may be increased to a desired, higher temperature range. In the desired temperature range, the target material may be ductile where the material is stronger and can withstand the shock up to the melting point of the target material relative to a focal spot on the target material where all beam energy is deposited. At the desired temperature range, a higher power may be used for the x-ray tube without degrading the target material. Use of a higher power may also result in an improved image quality for a diagnostic scan.

A desired range of temperature for a tungsten-alloy target may be between 200° C. and 300° C. After heating the target to the desired temperature range, the duration of time that the target remains within this range of temperature is a function of the cooling characteristics of the x-ray tube and of the frequency and nature of the exposures that deliver heat to the tube. As such, a thermal management system for the x-ray tube is designed to efficiently remove heat from the tube after an exposure is completed, to return the tube to below 300° C. However, if the tube is allowed to cool too fast for the desired patient throughput, the tube may be too cold to scan the next patient at the required power level.

Therefore, a tube conditioning procedure (also referred herein as tube warmup) may be desired to increase the tube temperature and maintain the temperature of the target in the desired temperature range before a diagnostic scan may be performed. An effective way to warm up the tube is to generate x-rays. A tube warmup procedure may typically consist of a pre-defined sequence of low-power, long exposures that may deliver sufficient energy over time to gradually warm up the target above brittle mode and into ductile mode. As such, an operator of the CT scanner may manually initiate a tube warmup before the patient enters the room in order to avoid unnecessary radiation exposure. In order to guarantee that the target is not in brittle mode, the same warmup sequence may be used regardless of an actual (initial) state of the tube.

However, if tube conditioning is to be manually initiated by the operator prior to each diagnostic scan, the conditioning process may cause an interruption in the workflow of the operator who attempts to carry out a maximum possible number of scans in a day. A warmup procedure may require an additional 3 to 5 minutes during which the patient will have to wait outside the room to avoid unnecessary radiation exposure. It would be challenging to maintain a high rate of completion of scans if this additional tube conditioning time is to be spent between every two consecutive patients.

If scanning is continued while the target temperature has decreased to below the desired temperature range, a loss of image quality performance may be observed since allowed exposures are power limited to protect the tube. Therefore, with a cooler tube, the recommended radiation dose for a desired image quality during a diagnostic scan may not be delivered.

The operator may have to manually initiate the tube warmup by using a tool separate from patient scanning. While the system provides information to the operator as to the state of the x-ray tube, tube conditioning may not always be part of the inherent workflow of the operator on the system. On the other hand, conditioning may not be automated since the operator needs to confirm that no one is in the scan room when x-rays are turned on even for the purpose of a tube warmup.

Using fixed, pre-defined exposure sequences for tube warmup that run open-loop may not allow control over the exact target temperature at the end of the warmup procedure. It is for instance possible to exceed the hot limit (e.g. 300° C.) at the time of the diagnostic scan. Some tools such as specific calibration steps (focal spot alignment, etc.) would also benefit from a desired target temperatures at the end of a warmup to produce consistent results. Diagnostic scanning would also benefit from running at temperatures that match the system environment when detailed calibration was initially performed and stored on the system. Repeatedly running long warmup sequences that deliver a lot of energy to the tube may be stressful to some tube components and reduce useful tube life. Therefore, new approaches are needed to overcome the above challenges centered on tube warmup consistency and ease-of-use.

Therefore, according to embodiments disclosed herein, a set of tube conditioning approaches may be carried out to effectively warmup the tube within a shorter time while preparing the subject (such as a patient) for the scan inside the scan room. The temperature of the x-ray tube may be controlled via a closed-loop control system. An initial thermal state of the tube, a desired thermal state of the tube, and duration of time available to reach the desired thermal state is used as input, and a thermal model of the tube behavior may be used to calculate the exposure parameters (such as voltage, current, duration of exposure) that is needed to transition the tube in the desired state. By considering the initial thermal state of the tube and using a closed-loop system, the final desired thermal state may be reached without overshooting the temperature. Different end thermal states may be selected a variety of scans (such diagnostic scanning planned at different times after tube warmup is completed, or different warmup outcomes for calibration procedures, etc.). By directly select the conditioning outcome, such as the amount of time from conditioning to subject scanning, it may be ensured that the tube target remains in the optimal temperature range at the time of the diagnostic exposure, which may vary across patient procedures, or at different times of the day with varied patient throughput, or across different shifts or teams of operators.

During x-ray generation for tube warmup, an x-ray blocking plate may be positioned in front of an exit (pre-patient) collimator aperture to completely block the primary x-ray beam path before the subject. In this way, the subject can be in the room being prepared for the diagnostic scan while x-ray generation may be continued for tube conditioning. By using the time for tube conditioning for subject preparation, overall time required for each subject may be reduced and more number of scans may be incorporated within a day.

One or more scout scans may be performed prior to a diagnostic scan. A higher power x-ray beam may be used during a scout scan to condition the x-ray tube for an immediately subsequent diagnostic scan. By adding a hardening filter in the path of the x-ray beam reaching the subject during a scout scan, the beam reaching the subject may be attenuated, thereby reducing the radiation exposure of the subject. Further, the beam collimation of the scout exposure may be significantly reduced (such as to a slit aperture) in order to reduce the portion of the x-ray beam that reaches the subject, thereby reducing the actual radiation dose received by the subject. In this way, a tube warmup can effectively be completed immediately before the diagnostic scan that typically follows the scout scan. This allows a seamless workflow where tube conditioning does not need to be manually performed outside of scan times. By conditioning the tube during an actual scan, focal spot position may be carried out consistently with reduced thermal motion, and better image quality may be achieved by matching the diagnostic scanning conditions to the way the system calibration vectors were initially generated. Tube warmup may also take less time since it is carried out immediately prior to the diagnostic scan exposure without much tube cool down time in between.

FIG. 7 shows a collimator blade assembly 700 including a collimator blade 702 and a blocking plate 704. The collimator blade 702 may be the collimator blade 408 or 410 in FIGS. 4A-4E. A blocking plate 704 may be attached to a lower surface of the collimator blade in the x-z plane with the x-ray beam incident on the collimator blade assembly 700 in the y-direction.

The blocking plate 704 may extend outside the edge of the collimator blade 702 in one direction. The extended portion of the blocking plate 704 may extend away from the edge of the collimator blade 702 forming an aperture for x-ray beam to pass through. As an example, the width of the blocking plate (x-direction) may be longer than the output port (opening) of the collimator such that the blocking plate 704 may be positioned to completely absorb any x-rays incident on the plate, thereby blocking radiation to pass through the output port. The length of the blocking plate 704 (z-direction) may be equal to the length of the collimator blade 702.

The blocking plate 704 may completely or partially overlap with the lower surface (base) of the collimator blade 702. In this example, the blocking plate 704 is in face sharing contact with the base of the collimator blade 702. In alternate embodiments, there may be a gap between the base of the collimator blade 702 and the blocking plate 704 with the blocking plate 704 placed between the collimator blade 702 and the output port of the collimator. The blocking plate 704 may be made of lead or tungsten to be able to absorb any direct or scattered x-ray beams that come in contact with it.

In this example, the upper surface (top) of the collimator blade 702 is shown to be curved which facilitates in obtaining a parallel beam profile for x-ray beams impinging on a detector. In alternate embodiments, the upper surface of the collimator blade 702 may be flat.

FIGS. 8A-8B show a collimation arrangement 812 for an x-ray beam including a blocking plate. An x-ray beam may pass through a gap (aperture) formed between a first collimator blade 802 and a second collimator blade 804 after passing through one or more filters (such as a bowtie filter and/or a hardening filter). As an example, the first collimator blade may be the first collimator blade 408 in FIGS. 4A-4E and/or collimator blade 702 in FIG. 7, and the second collimator blade may be second first collimator blade 410 in FIG. 4A-4E. After passing through the gap between the first collimator blade 802 and the second collimator blade 804, the x-ray beam may exit the collimator via a collimator output port (opening) 812. The gap between the first collimator blade 802 and the second collimator blade 804 may correspond to the desired beam diameter.

A first blocking plate 806 may be coupled to the base of the first collimator blade 802 and a second blocking plate 807 may be coupled to the base of the second collimator blade 804 to block any direct or scattered x-ray beam incident on it. The first blocking plate 806 may extend beyond the edge of the first collimator blade 802 to effectively block the x-ray beam when it is desired to block the entire x-ray beam from exiting the collimator via the output port.

FIG. 8A shows a first position 800 of the collimation arrangement 812. The collimation arrangement 812 may be in the first position when an x-ray beam is desired to exit the collimator and is used for scanning a subject.

The x-ray beam 806 is collimated to a desired size as it passes through an aperture 816 between the first collimator blade 802 and the second collimator blade 804. By adjusting the relative positioning of the first collimator blade 802 and the second collimator blade 804, the size of the aperture 816 may be adapted to the desired beam size. The collimated x-ray beam may then exit the collimator via the output port 812. FIG. 8B shows a second position 800 of the collimation arrangement 812.

FIG. 8B shows a second position 850 of the collimation arrangement 812. The collimation arrangement 812 may be in the second position when it is desired to block an x-ray beam from exiting the collimator such as during x-ray tube conditioning. During x-ray tube conditioning (warmup) x-ray may be generated to impart energy to the x-ray tube. However, in order to reduce radiation exposure of a subject prior to an actual scan, the x-ray may be blocked from exiting the collimator and reaching the subject being prepared for a subsequent scan.

One or both of the first collimator blade 802 and the second collimator blade 804 may be moved closest to each other such that the aperture (gap) 826 formed between the first collimator blade 802 and the second collimator blade 804 is the lowest possible and that one or more of the first collimator blade 802, the second collimator blade 804, the first blocking plate 806, and the second blocking plate 807 may completely block the x-ray beam 808 and any secondary (scattered) radiations 816.

In this example, the first collimator blade 802 along with the first blocking plate 806 is effectively being used to block the entire x-ray from reaching the output port 812 of the collimator. In this way, by attaching a separate blocking plate to the collimator blade and positioning the blocking plate in the path of the x-ray beam, the primary x-ray beam and scattered radiations may be blocked from reaching a subject. Therefore, during x-ray tube warmup, the subject may be prepared in the scanning room without the possibility of undesirable radiation exposure.

In this way, the systems of FIGS. 7 and 8A-B enable a system for an x-ray collimator including a first collimator blade and a second collimator blade separated by a gap, the gap forming an aperture of the collimator; and a blocking plate coupled to the first collimator blade, the blocking plate positioned in a path of an x-ray beam to block the x-ray beam from exiting the collimator during x-ray generation to condition a x-ray tube prior to a diagnostic scan.

Figure 9:
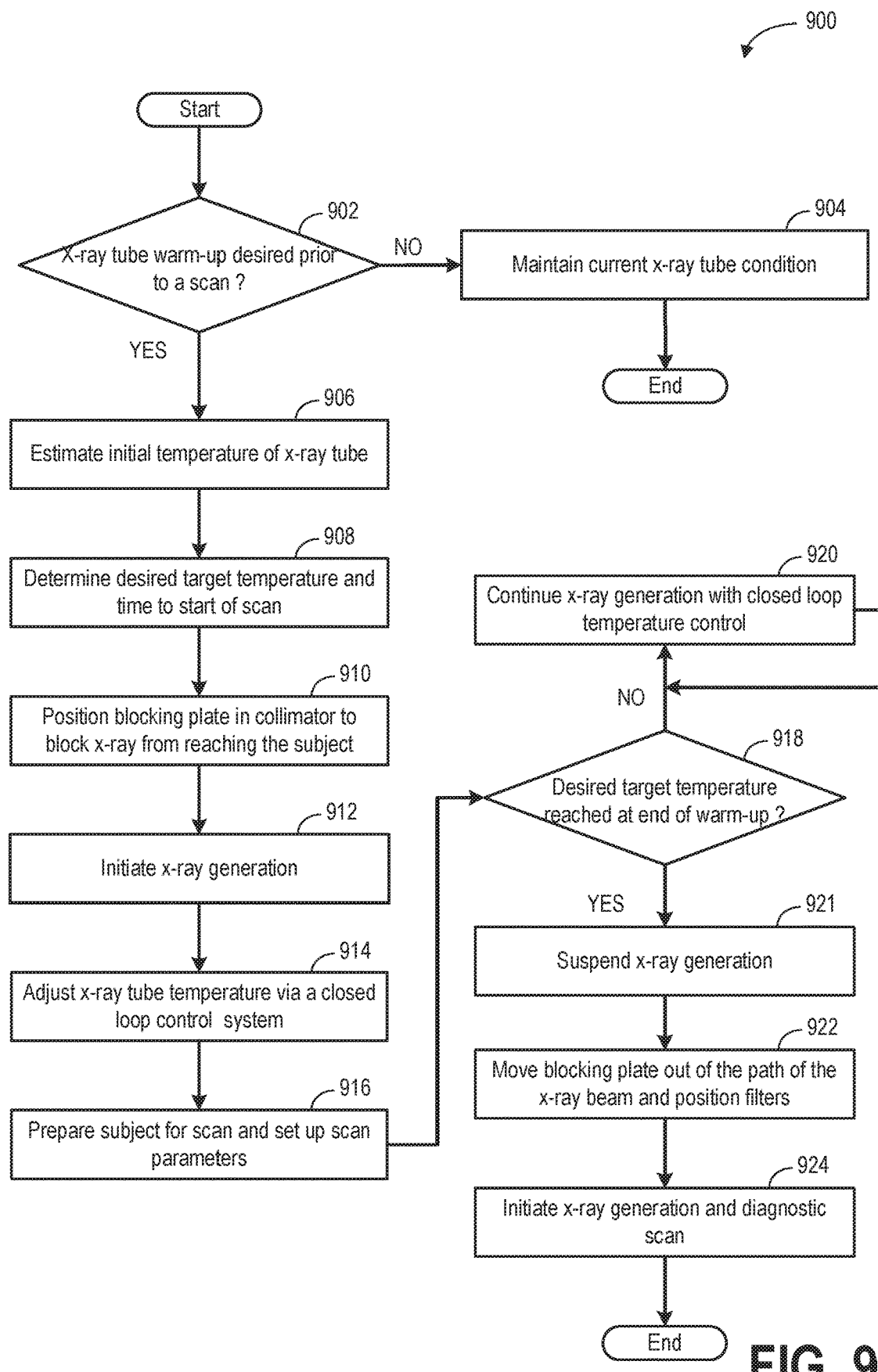
FIG. 9 shows a flow chart of an example method for conditioning an x-ray tube prior to a diagnostic scan.

FIG. 9 shows an example method 900 for conditioning an x-ray tube prior to a diagnostic scan. Method 900 may be carried out after completion of a diagnostic scan and/or upon receiving indication (such as via an operator) that another diagnostic scan is imminent.

At 902, the routine includes determining if x-ray tube warmup is desired prior to a scan. An x-ray tube warmup may include increasing the temperature of the x-ray tube and the x-ray target to a desired temperature range. In one example, the desired temperature range may be between 200° C. and 300° C. An x-ray tube warm up may be desired prior to a diagnostic scan so that the target material reaches a desired temperature range. Below the desired temperature range, the target material may be brittle whereby a high-energy electron beam impinging on the target may result in stress fractures such that a target failure might ensue. Use of a higher x-ray power during a scan may result in an improved image quality.

If it is determined that an x-ray tube warmup is not desired, at 904, the current x-ray tube condition may be maintained. In one example, in the current x-ray tube condition, x-rays may not be generated to actively heat the tube. In another example, x-ray generation in the x-ray tube may be continued without any alterations.

If it is determined that x-ray tube warmup is desired prior to a scan, at 806, an initial (current) temperature of the x-ray tube may be estimated. In one example, a thermal model may be used to estimate the initial temperature of the x-ray tube. The initial temperature may be molded based on ambient temperature, exposure history (such as power of x-ray generated in the tube) over a last calibrated duration (such as over last 5 hours), and thermal properties of the x-ray tube such as heat transfer coefficient of the tube and the target. The model may estimate a thermal state of the tube including a temperature of the target as the state evolves over time. As such the temperature of the target may be same as the temperature of the tube and other associated components. In another example, the target temperature may be different from that of the tube and a separate initial target temperature and initial tube temperature may be estimated. In another example, x-ray tube temperature may be estimated based on inputs from a temperature sensor housed in the x-ray tube.

At 908, a desired target temperature at the onset of the upcoming diagnostic scan and the time to the start of the scan may be determined. The desired target temperature at the start of the scan and the time remaining between the completion of the tube warmup routine and the start of the diagnostic scan may be termed as the end criteria. The end criteria may be built into some tools or system presets, or may be selected by the user. As an example, a user may input or select the desired temperature according to a scanning protocol or a menu. Also, the user may input the start time of the upcoming diagnostic scan.

In one example, for patient scanning, the user and/or the system may determine that the tube target should be above 200° C. five minutes after the completion of the warmup procedure. This may allow enough time to prepare the patient, position the anatomy and prepare for a contrast injection, while ensuring the target is still above brittle mode to avoid cold tube limits and allow the maximum available tube power for patient imaging. In another example, the user may want to extend the time to 200° C. (at the onset of the scan) to 10 minutes after the completion of the warmup procedure during conditions when more time is needed for a different patient or a procedure before the first diagnostic exposure. In yet another example, a calibration tool such as focal spot alignment may need the target to be at 330° C. one minute after tube warmup in order to align the spot for the average operating tube temperature, thus optimizing operation for patient scanning, and improving alignment consistency over time.

At 910, a blocking plate may be positioned in the collimator to block a collimator aperture. The blocking plate (such as blocking plate 806 in FIG. 8B) may be positioned in front of an exit (pre-patient) collimator aperture. The blocking plate may be made of tungsten which may absorb any x-ray radiations coming in contact with the plate, thereby inhibiting the radiation to reach the subject. The blocking plate may be positioned over an output port of the collimator completely blocking an aperture and the output port of the collimator, the aperture formed by a gap between a first collimator blade and a second collimator blade. The blocking plate may be coupled to a lower surface of one of the first collimator blade and the second collimator blade, the lower surface proximal to the output port of the collimator. The blocking plate may extend beyond a first edge of the base of the first collimator blade, wherein the first edge is distal from the second collimator blade.

The blocking plate may completely overlap the collimator output port and together with sufficient shielding in the collimator, indirect scattered and stray radiation escaping from the collimator assembly through the open port may be negligible. As such, the collimator blades may be designed to maintain a certain minimum aperture and not completely block the beam. Therefore, without the presence of the blocking plate, undesired scattered radiation may escape the collimator. Therefore, by using a separate blocking plate, x-ray beam may be completely blocked from reaching a subject during a tube warmup.

At 912, x-ray radiation may be initiated for tube warmup. For example, the radiation source (such as 104 of FIGS. 1-2) may be activated. The x-ray beam may be attenuated by the blocking plate before reaching a subject. The x-ray radiation is not being used for scanning. At 914, x-ray tube temperature may be adjusted by adjusting the x-ray radiation dosage via a closed loop system. The warmup end criteria (as determined in step 908) and the initial x-ray tube and x-ray target temperature may be used as input to a thermal management module. The thermal management module includes the model of the thermal state of the tube over time. Given the starting temperature condition and the thermal model for the x-ray tube, the thermal management module may calculate a specific sequence of warmup exposures that will result in the tube target meeting its temperature goal after the desired amount of time. The warmup sequence may be automatically tailored to the actual state of the tube relative to the end criteria. In one example, based on the initial target temperature, the module may determine a magnitude of power (in the form of tube voltage and current) to be delivered to the tube in order to provide sufficient energy desired for warming the tube to the desired temperature. The temperature of the target may be continually estimated during the warmup phase and the module may adjust the tube power based on the current temperature of the x-ray tube.

As an example, the power delivered to the x-ray tube may be decreased if the temperature increases at a faster rate while the tube power may be increased if the temperature increase rate lags. The thermal model of the x-ray tube is used by the module to predict the decrease in temperature in the time frame between the end of warmup and start of diagnostic scan, and the end temperature attained at the end of the warmup phase may be adjusted accordingly. The temperature reached at the end of the warmup phase may be higher than the desired temperature range of the diagnostic scan taking into account heat loss and reduction in temperature in the time duration between the end of warmup and start of the diagnostic scan. As an example, if a diagnostic scan at 200° C. is to be started five minutes after the end of the warmup period, the end temperature of the warmup period may be adjusted to 220° C. such that upon heat dissipation over the five minutes prior to the diagnostic scan (when active heating of the tube is discontinued), the temperature at the start of the diagnostic scan may be 200° C. In this way, by closed loop control of the x-ray tube conditioning, the desired temperature may be reached at the onset of the diagnostic scan.

By running tube warmup no longer than needed to meet a specific goal, system efficiency may be improved. Closed-loop control may also allow improved control of the end state (start of the diagnostic scan) precisely, thereby averting cold tube limits or tube cooling delays. Also unnecessary stress to the tube may be reduced that could otherwise receive more energy than necessary.

Even with an adaptive tube warmup, the operator may still need to initiate tube conditioning, as necessary, to avoid cold constraints. It would be desirable that the system supports a workflow where a manual tube warmup may be carried out independent of patient setup, or automatically as part of the normal workflow on the system.

While x-ray is being generated for tube conditioning, at 916, a subject (such as subject 204 in FIG. 2) of the imaging scans may be prepared for the upcoming diagnostic scan. The subject may be positioned on a motorized table (such as table 228 in FIG. 2). A table motor controller may move the table so that a proper section of the subject is within the gantry for imaging. A contrast agent may be injected into the imaging subject. The contrast agent may enhance the contrast of images captured specifically for certain anatomies. This step is optional and the diagnostic scan may be carried out without use of a contrast agent. Since the x-ray beam is shielded from reaching the subject, subject preparation may be carried out simultaneously with tube warmup without the radiation exposure to the subject.

While tube warmup, the scan parameters may be set up for carrying out a diagnostic scan. A user may input or select the scan parameters according to a scanning protocol or a menu. The scan parameters may include the type and sequence of the filters that are going to be used during the scan. The type of the filters may be chosen based on the anatomy of imaging subject that is to be imaged. The parameters may also include setting scan timing. As one example, the scan timing may include a start time and a duration for imaging each section. Anatomy information of the imaging subject may be loaded to the memory of the computation device. The anatomy information may be acquired from a pre-scan. The anatomy information may be acquired from the prior scout scan or a localized scan. This step may also include moving the imaging subject via the motorized table so that the proper section of the subject is within the gantry for imaging.

At 920, the routine includes determining if a desired target temperature has reached at the end of the warmup phase. As previously discussed, the desired target temperature at the end of the warmup phase may be higher than the desired temperature at the start of the diagnostic scan. If it is determined that the desired target temperature has not been reached at the end of the warmup period, at 920, x-ray generation may be continued with closed-loop control of the tube temperature.

If it is determined that the desired target temperature has reached at the end of the warmup phase, at 921, x-ray generation may be suspended by deactivating the radiation source. At 922, the blocking plate may be moved out of the path of the x-ray beam and filters to be used in the diagnostic scan may be moved into the path of the beam. A bowtie filter may be positioned in the path of the x-ray beam by operating a motor coupled to a carriage including the bowtie filter. The type of the filter may be determined based on the anatomy of the currently imaged section of the subject. The carriage may be moved along a shaft in a plane perpendicular to the plane of the x-ray beam to position the bowtie filter in the beam.

At 924, x-ray generation may be initiated by activating the radiation source and the diagnostic scan may commence according to the scan parameters set-up. In this way, prior to initiation of a diagnostic scan, a x-ray tube may be warmed up by generating x-ray in the x-ray tube, a power of the generated x-ray may be adjusted via a closed loop control of a temperature of the x-ray tube; and during the warm-up of the x-ray tube, a x-ray beam may be blocked from exiting a collimator by positioning a blocking plate in a path of the x-ray beam.

FIG. 10 shows a block diagram 1000 illustrating open-loop control of x-ray tube temperature prior to a scan. At 1002, an end criteria for an x-ray tube conditioning carried out prior to a scan may be defined either as an input by the user or by the system. The end criteria may include a temperature of the x-ray target at the onset of the upcoming scan and a time duration between the end of the tube conditioning (also referred herein as warmup) phase and the start of the subsequent scan.

Once the end criteria is defined, at 1004, the system may calculate an amount of energy to be delivered to the x-ray tube during the warmup phase to achieve the end criteria. In order to determine the amount of energy to be delivered, at 1012, the system enquires a current x-ray tube temperature via a thermal model and/or an x-ray tube temperature sensor. The system may use a look-up table to determine the amount of energy to be delivered with the current temperature and the end criteria as inputs and the amount of energy to be delivered to the x-ray tube as output.

At 1006, the system may transform the amount of energy to be delivered to the x-ray tube into specific x-ray warmup exposure(s). The energy may be imparted as a single, continuous, x-ray exposure or as a series of discrete x-ray exposures. The power delivered in each exposure may be estimated based on the amount of energy to be delivered to the x-ray tube and the duration of the exposure. Taking into account system constraints such as the maximum possible power that may be delivered to the x-ray tube, the system may determine the power delivered during the tube warmup phase based on a look-up table with the amount of energy to be delivered to the x-ray tube as input and the power to be delivered during each (or only) x-ray exposure.

At 1008, the user may activate a radiation source to generate x-rays in the tube. The power of the x-rays generated may impart the amount of energy desired to fulfil the end criteria. During the x-ray tube conditioning, a blocking plate may be placed within an x-ray beam collimator tube to stop the x-ray beam from reaching the patient. At 1010, the patient may be setup for the subsequent diagnostics scan and once the end criteria is reached, the diagnostics scan may be carried out. Alternatively, a calibration scan (with or without the presence of a patient) may also be carried out.

Once the scan is completed, the x-ray tube is immediately prepared for the subsequent scan of the same or next patient and the current x-ray tube temperature is enquired by the system to be used for closed-loop temperature control of the x-ray tube.

As described earlier, it is desired to attain an x-ray target temperature prior to a diagnostic scan. By operating below the desired thermal range, the x-ray tube target material may become brittle, thus leading to an increase in the number of fissures in the target and leading to degradation of the target. By operating above the desired thermal range, the system may overheat and cannot cool quickly enough at the time of the diagnostic scan. Operation of the x-ray tube outside the desired temperature range may result in reduced long-term reliability of the x-ray target material, leading to higher direct costs associated with servicing the tube, and higher indirect costs for the user and also reduction in the range of operating current values if the system is running either above or below the optimal operating range.

A typical conditioning procedure may dump thermal energy into the x-ray tube target, generally without consideration of the actual level of energy required to reach the optimal operating state. This can lead to restricted access to peak capability as the tube must cool down sufficiently from this excessively applied heat energy at the start of the actual diagnostic scan. For any CT-based procedure that involves scanning patient anatomy, the level of patient absorbed dose to x-ray radiation is critical to the consideration of the appropriateness of the procedure. During a scan or prior to it, appropriate measures may be undertaken to ensure that a radiation exposure of the patient does not exceed a pre-determined level.

One or more scout scans may be performed prior to a diagnostic scan. A higher power x-ray beam may be used during a scout scan to condition the x-ray tube for an immediately subsequent diagnostic scan.

Immediately prior to a scout scan, a targeted level of energy to reach the desired x-ray target temperature range may be provided as an input to a scan parameter optimizing algorithm. Further, a limit for radiation absorbed dose of the patient may be used as an input to the scan parameter optimizing algorithm. The algorithm may then adjust the scan parameters for the subsequent scout scan such that the targeted energy may be imparted to the x-ray tube to optimally condition the tube for the subsequent diagnostic scan while also exposing the patient to only the user-selected level of absorbed dose for the scout scan. By adding a hardening filter in the path of the x-ray beam reaching the subject during a scout scan, the beam reaching the subject may be attenuated, thereby reducing the radiation exposure of the subject. By using a higher powered beam during a scout scan, the image quality of the scout scan may be improved with key attributes of the scout mode also being maintained or improved, such as maintaining the ability to confidently prescribe a scan range for the subsequent diagnostic scan and maintain the contrast to noise ratio of the underlying scout image.

FIG. 11 shows example method 1100 for using a scout scan for conditioning an x-ray tube prior to a diagnostic scan. Method 1100 may be carried out after completion of a diagnostic scan and/or upon receiving indication (such as via an operator) that a diagnostic scan is imminent.

At 1102, the routine includes determining if x-ray tube warmup is desired prior to a scan. An x-ray tube warmup may include increasing the temperature of the x-ray tube and the x-ray target to a desired temperature range. In one example, the desired temperature range may be between 200° C. and 300° C. An x-ray tube warm up may be desired prior to a diagnostic scan so that the target material reaches a desired temperature range. Below the desired temperature range, the target material may be brittle whereby a high-energy electron beam impinging on the target may result in stress fractures such that a target degradation might ensue. Use of a higher x-ray power during a scan may result in an improved image quality.

If it is determined that an x-ray tube warmup is not desired, at 1104, the current x-ray tube condition may be maintained. In one example, in the current x-ray tube condition, x-rays may not be generated to actively heat the tube. In another example, x-ray generation in the x-ray tube may be continued without any alterations.

If it is determined that x-ray tube warmup is desired prior to a scan, at 1106, an allowable patient absorbed dose range may be received as input from an operator. The upper limit of the allowable absorbed dose range may correspond to a level of x-ray exposure that may not have any detrimental effect on the subject who is being scanned. As an example, an exposure level of an x-ray radiation coming in contact with the subject may be given by equation 1.

$$CTDI_{Vol} = \left(\frac{\text{Scout Power}}{\text{Cradle Power}}\right) * (CTDI_w^{Ref} * \text{Aperture}) \quad (1)$$

where $CTDI_{Vol}$ is the upper limit of the user defined range of allowable patient x-ray absorbed dose, $CTDI_w^{Ref}$ is the subject absorbed dose at a reference technique where $CTDI_w^{Ref}$ is based on a voltage (kV) in the x-ray tube, Scout power is a function of the voltage (kV) in the x-ray tube and the current (mA) in the x-ray tube, Cradle speed is the speed in mm/second of the bed on which the subject is positioned, and aperture is the beam aperture at system isocenter. As an example, patient exposure to radiation may be the patient absorbed dose or the radiation during during the scout scan (scout CTDIvol). The patient exposure may be different form that acquired by the CT system. At 1108, a number of scout scans to be performed prior to the diagnostic scan may be determined. The operator may input the number of scout scans desired via a keyboard or a touchscreen in the operator console. As an example, two scout scans may be carried out, one from a side and another from the front of a subject.

At 1110, a scan range for the scout scans may be determined. The time duration of the scout scan may be determined by the combination of the scan range and the cradle speed. As an example, the cradle may be able to move between a minimum speed and a maximum speed. The time duration of the scout scan may be a function of the cradle speed. The time duration of the scout scan may be highest at the lowest cradle speed. Therefore, the scan range may also set a maximum time duration of the scout scan.

At 1112, an initial (current) temperature of the x-ray tube may be determined along with a desired x-ray target temperature at the onset of the subsequent diagnostic scan (referred herein as final temperature). In one example, a thermal model may be used to estimate the initial temperature of the x-ray tube. The initial temperature may be molded based on ambient temperature, exposure history (such as power of x-ray generated in the tube) over a last calibrated duration (such as over last 5 hours), and thermal properties of the x-ray tube such as heat transfer coefficient of the tube and the target. The model may estimate a thermal state of the tube including a temperature of the target as the state evolves over time. As such the temperature of the target may be same as the temperature of the tube and other associated components. In another example, the target temperature may be different from that of the tube and a separate initial target temperature and initial tube temperature may be estimated. In another example, x-ray tube temperature may be estimated based on inputs from a temperature sensor housed in the x-ray tube.

The desired target temperature at the start of the scan and the time remaining between the completion of the scout scan and the start of the diagnostic scan may be termed as the end criteria. The end criteria may be built into some tools or system presets, or may be selected by the user. As an example, a user may input or select the desired temperature according to a scanning protocol or a menu. Also, the user may input the start time of the upcoming diagnostic scan.

In one example, for patient scanning, the user and/or the system may determine that the tube target should be above 200° C. five minutes after the completion of the scout scan. This may allow enough time to prepare the patient, position the anatomy and prepare for a contrast injection, while ensuring the target is still above brittle mode to avoid cold tube limits and allow the maximum available tube power for patient imaging. In another example, the user may want to extend the time to 200° C. (at the onset of the scan) to 10 minutes after the completion of the scout scan during conditions when more time is needed for a difficult patient or a procedure before the diagnostic exposure.

At 1114, an amount of energy to be imparted to the x-ray tube to attain the desired x-ray target temperature may be estimated based on the initial temperature and the desired x-ray target temperature at the onset of the subsequent diagnostic scan (final temperature). The desired amount of energy may be estimated as a function of the initial temperature, the final temperature, and a time duration between a completion of the scout scan(s) and the onset of the diagnostic scan. In one example, if two or more scout scans are successively carried out, the desired energy may be divided and imparted in two or more installments. The energy imparted to an x-ray tube during a scout scan may be given by equation 2.

$$\text{Energy} = \left(\frac{\text{Scout Power}}{\text{Cradle Power}}\right) * \text{Scout Length} \quad (2)$$

where energy is the amount of energy imparted to a x-ray tube during a scout scan, scout power is the mathematical product of the magnitudes of x-ray tube voltage and x-ray tube current, cradle speed is the speed in mm/second of the bed on which the subject is positioned, scout length is the total duration of the number of scout scans to be carried out. The scout length may be a function of the number of scout scans to be carried out and the duration of each scout scan.

At 1116, the scan parameter optimizing algorithm may be used to determine the scan parameters for the scout scan based on an allowable patient absorbed dose range (as determined in step 1106), the number of scout scans (as determined in step 1108), the scan range for each scout scan (as determined in step 1110), and the desired energy for x-ray target warm up (as determined in step 1114). The power to be provided to the tube for attaining the desired final thermal state is a function of the desired energy for x-ray tube warm up and the duration of the scout scan(s). The algorithm may estimate the power to be provided to the tube over the course of the scan(s) and determines current and voltage of the x-ray tube corresponding to the power. As such, different power levels provide different dosage of x-ray.

The scan parameters prescribed by the scan parameter optimizing algorithm based on the above mentioned inputs may include x-ray tube voltage (kV), x-ray tube current (kA), cradle speed during the scan (mm/sec), beam aperture at system isocenter, beam focal point size, scan field of view, the one or more filters to be used, etc. The scan parameter optimizing algorithm may automatically prescribe the scan parameters prior to the onset of the scout scan(s).

The scout scan parameters are tailored to match the energy demand of the system and patient absorbed dose limit as set by the user. To accomplish this the algorithm automatically selects the above mentioned scan parameters in order to match the system thermal input demand, user-selected absorbed dose range, and the independently set scan range, and produce a scout scan that meets the input energy target, within the patient absorbed dose range, over the course of the scan range. As an example, energy targets may be in the range of 25-400 kJ over all valid scout scan ranges 50-2000 mm. Acceptable (user set) patient absorbed dose levels may be in the range of 0.02 mGy-0.5 mGy. As an example, if the energy demand is 200 kJ, the scout scan range is independently set to 450 mm, and the user has chosen a scout CTDIvol range between 0.02-0.06 mGy, the algorithm may automatically select an x-ray tube voltage of 80 kV, an x-ray tube current of 555 mA, and a cradle speed of 100 mm/sec., resulting in an imparted energy of 200 kJ at an absorbed dose of 0.04 mGy. This example illustrates the mechanism behind how the algorithm chooses the system parameters to meet the dual targets of imparted energy and patient absorbed dose.

FIG. 12 shows a block diagram 1200 illustrating a guided selection of a scan protocol. A scan parameter optimizing algorithm 1202 may be used to determine scout scan parameters 1212. Inputs to the scan parameter optimizing algorithm 1202 may include a desired energy 1204 for attaining an optimal x-ray target temperature, a maximum permissible subject radiation absorbed dose level (or range) 1206, a scan range per scout scan 1210 such as a time duration of each scan, and a number of scout scans 1210 to be carried out for imparting the desired energy 1204. Based on the input, the scan parameter optimizing algorithm 1202 may optimize the power to be delivered during the course of each scout scan to be able to impart the desired level of energy over the entire duration of the scans. As an example, the algorithm may use a look-up table to determine the scout scan parameters 1212 as output based on the power to be delivered during each scan. The scout scan parameters automatically set by the algorithm 1202 may include x-ray tube voltage (kV), x-ray tube current (kA), cradle speed during the scan (mm/sec), beam aperture at system isocenter, beam focal point size, scan field of view, the one or more filters to be used, etc.

Returning to FIG. 11, at 1118, scout scan(s) may be initiated based on the scan parameters prescribed by the algorithm. Prior to generation of the x-ray beam for the scout scan, a bowtie filter and a hardening filter may be positioned in the path of the x-ray beam by operating a motor coupled to a carriage including the bowtie filter (such as bowtie filter 320 in FIG. 3) and the hardening filter (such as hardening filter 302 in FIG. 3). The carriage may be moved along a shaft in a plane perpendicular to the plane of the x-ray beam to position the bowtie filter and the hardening filter in the beam. The controller may actuate the motor to move the shaft and the carriage to the desired position. The hardening filter may intercept lower energy radiations to attenuating the beam, thereby decreasing the radiation exposure of the patient during the scout scan. By using the hardening filter, a higher powered x-ray beam may be used to heat the x-ray tube during the scout scan while maintaining the absorbed dose level of the subject within the user specified absorbed dose range. The hardening filter may at least partially overlap with the bowtie filter and the beam may first pass through the hardening filter and then enter the bowtie filter. Once the filters are positioned in the path of the beam, radiation source may be activated to generate x-rays. The dataset of the scout scan is acquired from the detector (such as 108 of FIG. 2) upon receiving the transmitted radiation signal from the imaging subject.

In this way, a carriage may include a hardening filter and one or more bowtie filters, and a filter driving system for moving the carriage to selectively position the hardening filter and one of the one or more bowtie filters in a path of a radiation beam between a radiation source and an imaging subject during a scout scan preceding a diagnostic scan, the scout scan carried out according to scan parameters computed based on a selected patient radiation absorbed dose limit and an amount of energy to be imparted to a x-ray tube of the radiation source for x-ray tube warmup.

At 1120, the routine includes determining if the scout scan has ended. The end of the scout scan may be determined based on the scan parameters determined by the algorithm at step 1116. If it is determined that the scout scan has not ended, at 1121, the scout scan may be continued to heat the x-ray tube. In one example, two or more scout scans may be carried out successively. The scan parameters for each scout scan may be prescribed by the algorithm.

If it is determined that the scout scan has ended, at 1122, the acquired dataset from the scout scan is displayed and stored. In one embodiment, dataset acquired from different sections of the subject may be re-constructed to form an image. The acquired dataset, as well as the processed images may be saved in the storage of the imaging system and no further scans may be carried out.

At 1122, x-ray generation may be initiated by activating the radiation source and the diagnostic scan may commence according to the scan parameters set-up. A bowtie filter may be positioned in the path of the x-ray beam by operating a motor coupled to a carriage including the bowtie filter. The hardening filter may be moved out of the path of the x-ray beam and at least one bowtie filter may be positioned in the path of the x-ray beam. The type of the filter may be determined based on the anatomy of the currently imaged section of the subject. For a diagnostic scan, a larger beam size is used and therefore a hardening filter may no longer be used. In one example, the bowtie filter used for the diagnostic scan may be same as the bowtie filter used in the scout scan. In another example, the bowtie filter used for the diagnostic scan may be different from the bowtie filter used in the scout scan. The carriage may be moved along a shaft in a plane perpendicular to the plane of the x-ray beam to position the bowtie filter in the beam.

In this way, prior to initiation of a diagnostic scan, user input may be received for each of a patient absorbed dose limit, duration of one or more scout scans preceding the diagnostic scan, a number of scout scans, a final temperature of an x-ray tube at the initiation of the diagnostic scan, an amount of energy to be imparted to a x-ray tube during the one or more scout scans may be estimated based on a current temperature of the x-ray tube temperature, the final temperature of the x-ray tube, and a time of initiation of the diagnostic scan, scan parameters for the one or more scout scans may be computed based on a patient absorbed dose limit and the amount of energy to be imparted to the x-ray tube during the one or more scout scans, a beam hardening filter may be positioned in a path of an x-ray beam, and the one or more scout scans may be performed according to the computed scan parameters to warm-up the x-ray tube.

FIG. 13 shows an example plot 1300 of variation in x-ray target temperature during a scout scan and a subsequent diagnostic scan. Line 1302 shows a variation in x-ray target temperature as estimated via a thermal model or output of a temperature sensor housed in the x-ray tube. For a diagnostic scan, the desired temperature range for the target is between temperature T2 and temperature T3.

A scout scan may be initiated at time t1. Prior to the scout scan, the temperature of the target may be between temperature T1 and temperature T2. If a diagnostic scan is carried out below temperature T2, the target material may be brittle whereby a high-energy electron beam impinging on the target may result in stress fractures such that a target degradation might ensue. During x-ray generating during a scout scan, at time t2, the temperature of the target may increase to above temperature T3. Carrying out a diagnostics scan above T3 may cause degradation of the x-ray tube.

By the time the diagnostics scan is carried out at time t3, the temperature of target may decrease to the optimal temperature range between T1 and T2 where the target material is ductile and a high-powered x-ray beam may be used for the diagnostic scan without any detrimental effects to the tube. As an example, T1 may be 100° C., t2 may be 200° C., and T3 may be 300° C.

In this way, the scan parameter optimizing algorithm may automatically prescribe several scan technique parameters (such as tube voltage, cradle speed, current, bowtie filter, x-ray beam aperture) of the scout scan to concurrently impart a targeted level of thermal energy to the x-ray tube system, while exposing the patient to a user-selected x-ray absorbed dose within a targeted absorbed dose range. This algorithm accomplishes this dual task while improving the image quality of the scout scan during a procedure that is part of routine patient workflow. Optimal thermal conditions of the x-ray tube during a diagnostic scan translates directly to increased reliability of the x-ray tube leading to a concurrent reduction in commercial costs of replacement and an increase in customer satisfaction.

By thermally conditioning the x-ray tube prior to a diagnostic scan, maximum power capability of the CT system may be used during scans and consistency of diagnostic image quality will therefore be improved. Use of a scout scan for x-ray tube conditioning may reduce or negate the need for separate and additional out of room tube warmups that occur during a standard day of scanning workflow, sometimes as part of the patient scanning schedule, where the timing needs to be managed by a CT technologist, thereby improving workflow.

In one example, an imaging system, comprises: a carriage including one or more hardening filters and one or more bowtie filters, and a filter driving system for moving the carriage to selectively position the one or more hardening filters and the one of the one or more bowtie filters in a path of a radiation beam between a radiation source and an imaging subject, the one or more hardening filters at least partially overlapping with at least one of the one or more bowtie filters. In the preceding example method, additionally or optionally, the one or more hardening filter only partially overlaps with each of the one or more bowtie filters. In any or all of the preceding examples, additionally or optionally, the one or more bowtie filters include a first bowtie filter and a second bowtie placed adjacent to each other within the carriage. In any or all of the preceding examples, additionally or optionally, the one or more filters are placed between the first bowtie filter and the second bowtie filter, the one or more hardening filters partially overlapping with each of the first bowtie filter and the second bowtie filter. In any or all of the preceding examples, additionally or optionally, the first bowtie filter is housed within a first slot formed in a cavity of the carriage and wherein the second bowtie filter is housed within a second slot formed in the cavity of the carriage, the first slot separated from the second slot via a tab. In any or all of the preceding examples, additionally or optionally, the one or more hardening filters are embedded within a recess between the first bowtie filter and the second bowtie filter, the one or more hardening filters coupled to the tab. In any or all of the preceding examples, additionally or optionally, each of the one or more hardening filters include a support structure and one or more metallic sheets, the support structure and the one or more metallic sheets stacked together and coupled to the tab via a plurality of bolts. In any or all of the preceding examples, additionally or optionally, the support structure and the one or more metallic sheets may be of a same dimension, the support structure made of a material different from that of the one or more metallic sheets.

The system of claim 5, further comprising, an aluminum filter coupled to an underside of the carriage. In any or all of the preceding examples, additionally or optionally, the radiation beam passed through the one or more hardening filters, then one of the one or more bowtie filters, and the aluminum filter prior to entering the imaging subject. In any or all of the preceding examples, additionally or optionally, the filter driving system includes a motor coupled to the carriage via a shaft, the motor operated to translate the shaft for positioning the one or more hardening filters and the one of the one or more bowtie filters in the path.

Another example method for an imaging system comprises: during a first imaging, moving a carriage to position a hardening filter and a first bowtie filter housed in the carriage in a path of a radiation beam between a radiation source and an imaging subject, and during a second imaging, moving the carriage to move the hardening filter and the first bowtie filter out of the path of the radiation and then position a first bowtie filter or a second bowtie filter housed in the carriage in the path of the radiation. In the preceding example method, additionally or optionally, the first imaging is a scout scan and a second imaging is a diagnostic scan of an anatomy of the imaging subject, a beam size used in the first imaging smaller than a beam size used in the second imaging. In any or all of the preceding examples, additionally or optionally, the moving the carriage includes actuating a motor coupled to the carriage via a shaft, the shaft translating in a direction perpendicular to a direction of the path of the radiation to position one or more of the hardening filter, the first bowtie filter, and the second bowtie filter in the path of the radiation. In any or all of the preceding examples, additionally or optionally, each of the first bowtie filter and the second bowtie filter are positioned inside corresponding, adjacent slots within the carriage and the hardening filter is coupled to the carriage between the first bowtie filter and the second bowtie filter. In any or all of the preceding examples, additionally or optionally, the hardening filter partially overlaps with each of the first bowtie filter and the second bowtie filter, and herein, during the first imaging, the radiation beam first passes through the hardening filter and then passes through the first bowtie filter.

In yet another example, a system for an imaging system, comprises: a gantry for receiving an imaging subject, a radiation source positioned in the gantry for emitting radiation exposure, a detector positioned on the opposite of the gantry relative to the radiation source, a motorized table for moving the imaging subject within the gantry, a computation device with instructions stored in a non-transient memory, a first bowtie filter, a second bowtie filter, and one or more hardening filters positioned in the filter carriage, the one or more hardening filters mounted in between the first bowtie filter and the second bowtie filter and partially overlapping with each of the first bowtie filter and the second bowtie filter, and a filter driving system for switching filters by moving one or more of the first bowtie filter, the second bowtie filter, and the one or more hardening filters into or out of the radiation beam. In the preceding example system, additionally or optionally, each of the first bowtie filter and the second bowtie filter include a first, straight long side and a second, parallel long side including a central ridge, each of the first bowtie filter and the second bowtie filter made of graphite. In any or all of the preceding examples, additionally or optionally, the hardening filter includes each of a rectangular support structure, and one or more rectangular metallic sheets stacked under the support structure. In any or all of the preceding examples, additionally or optionally, the rectangular support structure is made of aluminum and the one or more rectangular metallic sheets are made of copper with each of the one or more rectangular metallic sheets having a different thickness.

FIGS. 1-5D, 7, and 8A-8B show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space there-between and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. An imaging system, comprising:
a first bowtie filter, a second bowtie filter, and a hardening filter;
a carriage that includes the first bowtie filter and the hardening filter;
a first motor coupled to the carriage and a second motor coupled to the second bowtie filter,
wherein the first motor is configured to move the carriage to selectively position at least one of the hardening filter and the first bowtie filter in a path of a radiation beam between a radiation source and an imaging subject, and
wherein the second motor is configured to move the second bowtie filter into the path of the radiation beam.

2. The system of claim 1, further comprising:
a third bowtie filter,
wherein the carriage further includes the third bowtie filter, and
wherein the beam hardening filter overlaps with one of the first bowtie filter and the third bowtie filter.

3. The system of claim 1, wherein the beam hardening filter overlaps with both of the first bowtie filter and the third bowtie filter.

4. The system of claim 3, wherein the first bowtie filter and the third bowtie filter are placed between the first bowtie filter and the third bowtie filter, the hardening filter partially overlapping with each of the first bowtie filter and the third bowtie filter.

5. The system of claim 3, wherein the first bowtie filter is housed within a first slot formed in a cavity of the carriage and wherein the third bowtie filter is housed within a second slot formed in the cavity of the carriage, the first slot separated from the second slot via a tab.

6. The system of claim 5, wherein the hardening filter is embedded within a recess between the first bowtie filter and the third bowtie filter, and coupled to the tab.

7. The system of claim 5, wherein the hardening filter includes a support structure and one or more metallic sheets, the support structure and the one or more metallic sheets stacked together and coupled to the tab via a plurality of bolts.

8. The system of claim 7, wherein the support structure and the one or more metallic sheets may be of a same dimension, the support structure made of a material different from that of the one or more metallic sheets.

9. The system of claim 5, further comprising, an aluminum filter coupled to an underside of the carriage.

10. The system of claim 9, wherein the radiation beam passed through the hardening filter, then one of the bowtie filters, and the aluminum filter prior to entering the imaging subject.

11. The system of claim 1, further comprising:
a first shaft coupled to the first motor and the carriage; and
a second shaft coupled to the second motor and the second bowtie filter,
wherein the first motor is configured to translate the shaft for positioning at least one of the hardening filter and the first bowtie filter in the path of the radiation beam.

12. A method for an imaging system, comprising:
during a first imaging, moving a carriage to position a hardening filter and a first bowtie filter housed in the carriage in a path of a radiation beam between a radiation source and an imaging subject, and
during a second imaging, moving the carriage to move the hardening filter and the first bowtie filter out of the path of the radiation and then positioning a second bowtie filter in the path of the radiation,
wherein the carriage does not include the second bowtie filter.

13. The method of claim 12, wherein the first imaging is a scout scan and a second imaging is a diagnostic scan of an anatomy of the imaging subject.

14. The method of claim 12, wherein the moving the carriage includes actuating a motor coupled to the carriage via a shaft, the shaft translating in a direction perpendicular to a direction of the path of the radiation to position at least one of hardening filter and the first bowtie filter in the path of the radiation.

15. The method of claim 12, wherein the carriage further houses:
a third bowtie filter,
wherein the first bowtie filter and the third bowtie filter are positioned inside corresponding, adjacent slots within the carriage and the hardening filter is coupled to the carriage between the first bowtie filter and the second bowtie filter.

16. The method of claim 15, wherein the hardening filter partially overlaps with each of the first bowtie filter and the third bowtie filter, and herein, during the first imaging, the radiation beam first passes through the hardening filter and then passes through the first bowtie filter.

17. An imaging system, comprising:
a gantry for receiving an imaging subject;
a radiation source positioned in the gantry for emitting radiation exposure;
a detector positioned on the opposite of the gantry relative to the radiation source;
a motorized table for moving the imaging subject within the gantry;
a computation device with instructions stored in a non-transient memory;
a first bowtie filter, a second bowtie filter, and one or more hardening filters positioned in the filter carriage, the one or more hardening filters mounted in between the first bowtie filter and the second bowtie filter and partially overlapping with each of the first bowtie filter and the second bowtie filter;
a third bowtie filter positioned outside of the filter carriage;
a first filter driving system configured to move one or more of the first bowtie filter, the second bowtie filter, and the one or more hardening filters into or out of the radiation beam; and
a second filter driving system configured to move the third bowtie filter into or out of the radiation beam.

18. The system of claim 17, wherein each of the first bowtie filter and the second bowtie filter include a first, straight long side and a second, parallel long side including a central ridge, each of the first bowtie filter and the second bowtie filter made of graphite.

19. The system of claim 17, wherein the hardening filter includes each of a rectangular support structure, and one or more rectangular metallic sheets stacked under the support structure.

20. The system of claim 19, wherein the rectangular support structure is made of aluminum and the one or more rectangular metallic sheets are made of copper with each of the one or more rectangular metallic sheets having a different thickness.

* * * * *